US012060580B2

(12) United States Patent
Little et al.

(10) Patent No.: US 12,060,580 B2
(45) Date of Patent: Aug. 13, 2024

(54) RENAL PROGENITOR CELLS

(71) Applicant: The University of Queensland, Queensland (AU)

(72) Inventors: Melissa Little, Queensland (AU); Minoru Takasato, Toowong Queensland (AU)

(73) Assignee: The University of Queensland, Queensland (AU)

(*) Notice: Subject to any disclaimer, the term of this patent is extended or adjusted under 35 U.S.C. 154(b) by 700 days.

(21) Appl. No.: 17/155,631

(22) Filed: Jan. 22, 2021

(65) Prior Publication Data

US 2021/0371826 A1 Dec. 2, 2021

Related U.S. Application Data

(62) Division of application No. 14/898,213, filed as application No. PCT/AU2014/000608 on Jun. 13, 2014, now Pat. No. 10,900,022.

(30) Foreign Application Priority Data

Jun. 14, 2013 (AU) ................................ 2013902215
Nov. 27, 2013 (AU) ................................ 2013904580

(51) Int. Cl.
*C12N 5/071* (2010.01)
*G01N 33/50* (2006.01)

(52) U.S. Cl.
CPC ....... *C12N 5/0687* (2013.01); *G01N 33/5014* (2013.01); *G01N 33/5044* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2501/91* (2013.01); *C12N 2506/02* (2013.01); *C12N 2506/45* (2013.01)

(58) Field of Classification Search
CPC ........ C12N 2501/119; C12N 2501/155; C12N 2501/16; C12N 2501/385; C12N 2501/415; C12N 2501/91; C12N 2506/02; C12N 2506/45; C12N 5/0687; G01N 33/5014; G01N 33/5044; A61P 13/12
See application file for complete search history.

(56) References Cited

U.S. PATENT DOCUMENTS

| 6,417,185 B1 | 7/2002 | Goff et al. |
| 6,477,783 B1 | 11/2002 | Harman et al. |
| 6,489,344 B1 | 12/2002 | Nuss et al. |
| 6,517,872 B1 | 2/2003 | Yayon et al. |
| 7,005,252 B1 | 2/2006 | Thomson |
| 7,037,918 B2 | 5/2006 | Nuss et al. |
| 7,045,519 B2 | 5/2006 | Nuss et al. |
| 7,326,570 B2 | 2/2008 | Nigam et al. |
| 7,425,557 B2 | 9/2008 | Nuss et al. |
| 7,439,064 B2 | 10/2008 | Thomson et al. |
| 8,148,149 B2 | 4/2012 | Nigam et al. |
| 8,263,403 B2 | 9/2012 | Perry et al. |
| 8,278,105 B2 | 10/2012 | Pera et al. |
| 8,431,395 B2 | 4/2013 | Ying et al. |
| 8,518,700 B2 | 8/2013 | You et al. |
| 8,546,140 B2 | 10/2013 | Mack et al. |
| 8,569,061 B2 | 10/2013 | Nistor |
| 8,597,947 B2 | 12/2013 | Reubinoff |
| 8,906,677 B2 | 12/2014 | Li et al. |
| 8,951,798 B2 | 2/2015 | Palecek et al. |
| 8,962,322 B2 | 2/2015 | Shi et al. |
| 9,074,180 B2 | 7/2015 | Smith et al. |
| 9,080,145 B2 | 7/2015 | Nelson |
| 2006/0177925 A1 | 8/2006 | Rosenberg et al. |
| 2010/0317104 A1 | 12/2010 | Elefanty et al. |
| 2012/0149110 A1 | 6/2012 | Kitamura et al. |
| 2012/0207744 A1 | 8/2012 | Mendlein et al. |

(Continued)

FOREIGN PATENT DOCUMENTS

| CN | 103555660 A | 2/2014 |
| EP | 3020803 A1 | 5/2016 |

(Continued)

OTHER PUBLICATIONS

Takasato et al., ""Directing human embryonic stem cell differentiation towards a renal lineage generates a self-organizing kidney,"" Nature Cell Biology, Dec. 15, 2013, vol. 16, No. 1, pp. 118-127.
Astashkina et al., "A 3-D organoid kidney culture model engineered for high-throughput nephrotoxicity assays," Biomaterials, Jun. 2012, vol. 33, No. 18, pp. 4700-4711.
Barak et al., "FGF9 and FGF20 Maintain the Stemness of Nephron Progenitors in Mice and Man", Developmental Cell, Jun. 12, 2012, vol. 22, No. 6 pp. 1191-1207.
Batchelder et al., "Renal ontogeny in the rhesus monkey (*Macaca mulatta*) and directed differentiation of human embryonic stem cells toward kidney precursors," Differentiation, Jul. 2009, vol. 78, pp. 45-56.
Beattie et al., "Activin A Maintains Pluripotency of Human Embryonic Stem Cells in the Absence of Feeder Layers," Stem Cells, Apr. 2005, vol. 23, pp. 489-495.

(Continued)

*Primary Examiner* — Shin Lin Chen
*Assistant Examiner* — Khoa Nhat Tran
(74) *Attorney, Agent, or Firm* — Leon Y. Lum

(57) ABSTRACT

A method is provided for simultaneously producing both nephron progenitor cells and ureteric epithelial progenitor cells including the step of contacting intermediate mesoderm cells with: fibroblast growth factor 9 and/or fibroblast growth factor 20 and optionally, one or more selected from the group consisting of: bone morphogenic protein 7; heparin; a Wnt agonist; retinoic acid; and an RA antagonist. The concentrations of Wnt agonist, retinoic acid and/or RA antagonist may be manipulated to favour the relative production of nephron progenitor cells and ureteric epithelial progenitor cells. The intermediate mesoderm cells are ultimately derived from human pluripotent stem cells via a posterior primitive streak stage. The nephron progenitor cells and ureteric epithelial progenitor cells may have end uses such as for kidney repair and regeneration, bioprinting of kidneys and screening compounds for nephrotoxicity.

18 Claims, 21 Drawing Sheets
(15 of 21 Drawing Sheet(s) Filed in Color)
Specification includes a Sequence Listing.

(56) References Cited

U.S. PATENT DOCUMENTS

| | | |
|---|---|---|
| 2013/0059325 A1 | 3/2013 | Dekel |
| 2014/0363888 A1 | 12/2014 | Osafune et al. |
| 2015/0037883 A1 | 2/2015 | Baharvand et al. |
| 2015/0079675 A1 | 3/2015 | Li et al. |
| 2015/0087058 A1 | 3/2015 | Nam |
| 2015/0118748 A1 | 4/2015 | Ra et al. |

FOREIGN PATENT DOCUMENTS

| | | |
|---|---|---|
| WO | 03046141 A2 | 6/2003 |
| WO | 2005075636 A1 | 8/2005 |
| WO | 2012011610 A1 | 1/2012 |
| WO | 2014197934 A1 | 12/2014 |
| WO | 2014200115 A1 | 12/2014 |

OTHER PUBLICATIONS

Blank et al., "BMP7 promotes proliferation of nephron progenitor cells via a JNK-dependent mechanism", Development, Aug. 2009, vol. 136, pp. 3557-3566.

Bruce et al., "In vitro differentiation of murine embryonic stem cells toward a renal lineage," Differentiation, Jun. 2007, vol. 75, No. 5, pp. 337-349.

Colvin et al., "Genomic Organization and Embryonic Expression of the Mouse Fibroblast Growth Factor 9 Gene", Developmental Dynamics, Sep. 21, 1999, vol. 216, pp. 72-88.

D'Amour et al., "Efficient differentiation of human embryonic stem cells to definitive endoderm", Nature Biotechnology, Oct. 28, 2005, vol. 23, No. 12, pp. 1534-1541.

Fakhry et al., "Effects of FGF-2/-9 in calvarial bone cell cultures: differentiation stage-dependent mitogenic effect, inverse regulation of BMP-2 and noggin, and enhancement of osteogenic potential," Bone, 2005, vol. 36, pp. 254-266.

James et al., "Bmp signaling promotes intermediate mesoderm gene expression in a dose-dependent, cell-autonomous and translation-dependent manner", Developmental Biology, Dec. 2005, vol. 288, pp. 113-125.

Kenji Osafune, "Kidney regeneration and disease modeling research using iPS cell technology," Nihon Shoni Jinzobyo Gakkai Zasshi, 2013, vol. 26, No. 1, pp. 64-69.

Little et al., "Understanding kidney morphogenesis to guide renal tissue regeneration," Nature Reviews Nephrology, Aug. 30, 2016, vol. 12, pp. 624-635.

Little et al., "Generating a self-organizing kidney from2 pluripotent cells," Current Opinion in Organ Transplantation, Apr. 2015, vol. 20, No. 2, pp. 178-186.

Metsuyanim et al., "Expression of Stem Cell Markers in the Human Fetal Kidney," PLoS One, Aug. 21, 2009, vol. 4, No. 8, p. e6709, 15 pages.

Miyamoto et al., "Molecular Cloning of a Novel Cytokine cDNA Encoding the Ninth Member of the Fibroblast Growth Factor Family, Which Has a Unique Secretion Property," Molecular and Cellular Biology, Jul. 1993, vol. 13, No. 7, pp. 4251-4259.

Morizane et al., "Differentiation of murine embryonic stem and induced pluripotent stem cells to renal lineage in vitro", Biochem Biophys Res Commun, Dec. 2009, vol. 390, pp. 1334-1339.

Ng et al., "A protocol describing the use of a recombinant protein-based, animal product-free medium (APEL) for human embryonic stem cell differentiation as spin embryoid bodies," Nature Protocols, Apr. 2008, vol. 3, No. 5, pp. 768-776.

Ornitz et al., "Ligand Specificity and Heparin Dependence of Fibroblast Growth Factor Receptors 1 and 3," The Journal of Biological Chemistry, Aug. 1992, vol. 267, No. 23, pp. 16305-16311.

Schuldiner et al., "Effects of eight growth factors on the differentiation of cells derived from human embryonic stem cells," PNAS, Oct. 2000, vol. 97 pp. 11307-11312.

Shoufu et al., "Experimental Study on Differentiation of Embryonic Stem Cell into Renal Progenitor Cells with Cell Growth Factors," Chinese Journal of Integrated Traditional and Western Nephrology, Dec. 2012, vol. 13, No. 12, pp. 1058-1063.

Supplemental European Search Report for European Application No. EP 14 81 0526, dated Dec. 23, 2016 in 11 pages.

Taguchi, A., et al., "Redefining the In Vivo Origin of Metanephric Nephron Progenitors Enables Generation of Complex Kidney Structures from Pluripotent Stem Cells," Cell Stem Cell, Jan. 2014, vol. 14, pp. 53-67.

Takasato et al., "Generating kidney organoids from human pluripotent stem cells," Nature Protocols, Aug. 18, 2016, vol. 11, No. 9, pp. 1681-1692.

Takasato et al., "The origin of the mammalian kidney: implications for recreating the kidney in vitro," Development, Jun. 2015, vol. 142, pp. 1937-1947.

Trueb et al., "Role of FGFRL1 and other FGF signaling proteins in early kidney development," Cell. Mol. Life Sci., Oct. 2012, vol. 70, pp. 2505-2518.

Yasuo et al., "FGF8/17/18 functions together with FGF9/16/20 during formation of the notochord in Ciona embryos", Developmental Biology, Sep. 2006, vol. 302, pp. 92-103.

Zhang et al., "Short-term BMP-4 treatment initiates mesoderm induction in human embryonic stem cells," Blood, Feb. 2008, vol. 111, No. 4, pp. 1933-1941.

Toyohara, et al., "Development of Differentiation Methods From Human IPSCS/ESCS Into Nephron Progenitor Cells," International Society for Stem Cell Research Poster Abstracts, Jun. 2013, Abstract No. F-2184, 3 pages.

International Search Report for International Application No. PCT/AU2014/000608, Australian Patent Office, Australia, dated Jul. 23, 2014, 3 pages.

Galceran, "Wnt3a−/−−like phenotype and limb deficiency in Lef1(−/−)Tcf1(−/−) mice", Gene & Development, Mar. 1999, vol. 13, pp. 709-717.

Barak et al., "FGF9 and FGF20 Maintain the Stemness of Nephron Progenitors in Mice and Man—Supplemental Information", Developmental Cell, Jun. 12, 2012, pp. 1-9.

Vainio, "How the Developing Mammalian Kidney Assembles Its Thousands of Nephrons: Fgfs as Stemness Signals", Developmental Cell, Jun. 12, 2012, vol. 22, No. 6, pp. 1125-1126.

Narayanan et al., "Human embryonic stem cells differentiate into functional renal proximal tubular-like cells", Kidney International, Apr. 2013, vol. 83, No. 4, pp. 593-603.

Strait, "Clues found to way embryonic kidney maintains its fleeting stem cells", Washington University School of Medicine, Jun. 11, 2012, pp. 1-4.

SEQUENCE LISTING

<160> NUMBER OF SEQ ID NOS: 76

<210> SEQ ID NO 1
<211> LENGTH: 20
<212> TYPE: DNA
<213> ORGANISM: Homo sapiens

<400> SEQUENCE: 1
tatgcactgc aaagcagacc                                          20

<210> SEQ ID NO 2
<211> LENGTH: 20
<212> TYPE: DNA
<213> ORGANISM: Homo sapiens

<400> SEQUENCE: 2
atgcaacctg accgagaagt                                          20

<210> SEQ ID NO 3
<211> LENGTH: 20
<212> TYPE: DNA
<213> ORGANISM: Homo sapiens

<400> SEQUENCE: 3

```
ttcagctaaa gccccagaga                                               20

<210> SEQ ID NO 4
<211> LENGTH: 19
<212> TYPE: DNA
<213> ORGANISM: Homo sapiens

<400> SEQUENCE: 4
ggtaccccga catccactt                                                19

<210> SEQ ID NO 5
<211> LENGTH: 20
<212> TYPE: DNA
<213> ORGANISM: Homo sapiens

<400> SEQUENCE: 5
aggtacccaa ccctgaggag                                               20

<210> SEQ ID NO 6
<211> LENGTH: 20
<212> TYPE: DNA
<213> ORGANISM: Homo sapiens

<400> SEQUENCE: 6
ccgcacacgg ctgcatgaga                                               20

<210> SEQ ID NO 7
<211> LENGTH: 20
<212> TYPE: DNA
<213> ORGANISM: Homo sapiens

<400> SEQUENCE: 7
cgatgcaggg cttgtacccc                                               20

<210> SEQ ID NO 8
<211> LENGTH: 23
<212> TYPE: DNA
<213> ORGANISM: Homo sapiens

<400> SEQUENCE: 8
gccgaggcca aggaaaggga gaa                                           23

<210> SEQ ID NO 9
<211> LENGTH: 20
<212> TYPE: DNA
<213> ORGANISM: Homo sapiens

<400> SEQUENCE: 9
cgcacggtgt cttcagaggc                                               20

<210> SEQ ID NO 10
<211> LENGTH: 20
<212> TYPE: DNA
<213> ORGANISM: Homo sapiens

<400> SEQUENCE: 10
ctgcctggtg ctgctccaca                                               20

<210> SEQ ID NO 11
<211> LENGTH: 20
<212> TYPE: DNA
<213> ORGANISM: Homo sapiens
```

-continued

```
<400> SEQUENCE: 11
ccacggtcaa ctcgggacct                                                 20

<210> SEQ ID NO 12
<211> LENGTH: 20
<212> TYPE: DNA
<213> ORGANISM: Homo sapiens

<400> SEQUENCE: 12
ggcaacctac gcaagatggc                                                 20

<210> SEQ ID NO 13
<211> LENGTH: 20
<212> TYPE: DNA
<213> ORGANISM: Homo sapiens

<400> SEQUENCE: 13
tctaccatgg ctacctgcct                                                 20

<210> SEQ ID NO 14
<211> LENGTH: 20
<212> TYPE: DNA
<213> ORGANISM: Homo sapiens

<400> SEQUENCE: 14
gagtatgagt gccaggtcgg                                                 20

<210> SEQ ID NO 15
<211> LENGTH: 20
<212> TYPE: DNA
<213> ORGANISM: Homo sapiens

<400> SEQUENCE: 15
gccgtgacct tggtggctca                                                 20

<210> SEQ ID NO 16
<211> LENGTH: 22
<212> TYPE: DNA
<213> ORGANISM: Homo sapiens

<400> SEQUENCE: 16
tctgctccat gagatcacgc ca                                              22

<210> SEQ ID NO 17
<211> LENGTH: 22
<212> TYPE: DNA
<213> ORGANISM: Homo sapiens

<400> SEQUENCE: 17
cttcacgagc agaggtcata cc                                              22

<210> SEQ ID NO 18
<211> LENGTH: 22
<212> TYPE: DNA
<213> ORGANISM: Homo sapiens

<400> SEQUENCE: 18
tacggttctg gctcacaaag gg                                              22

<210> SEQ ID NO 19
<211> LENGTH: 20
<212> TYPE: DNA
<213> ORGANISM: Homo sapiens
```

```
<400> SEQUENCE: 19
cgagatccct ccaaaatcaa                                           20

<210> SEQ ID NO 20
<211> LENGTH: 20
<212> TYPE: DNA
<213> ORGANISM: Homo sapiens

<400> SEQUENCE: 20
gaaaggctgc tgaactttgg                                           20

<210> SEQ ID NO 21
<211> LENGTH: 19
<212> TYPE: DNA
<213> ORGANISM: Homo sapiens

<400> SEQUENCE: 21
caggtcgcta ggggagatg                                            19

<210> SEQ ID NO 22
<211> LENGTH: 20
<212> TYPE: DNA
<213> ORGANISM: Homo sapiens

<400> SEQUENCE: 22
cggcactttg gagaaagaag                                           20

<210> SEQ ID NO 23
<211> LENGTH: 20
<212> TYPE: DNA
<213> ORGANISM: Homo sapiens

<400> SEQUENCE: 23
ttcagagaga ggggaacagg                                           20

<210> SEQ ID NO 24
<211> LENGTH: 20
<212> TYPE: DNA
<213> ORGANISM: Homo sapiens

<400> SEQUENCE: 24
gatgggtgag gggtgtgtag                                           20

<210> SEQ ID NO 25
<211> LENGTH: 20
<212> TYPE: DNA
<213> ORGANISM: Homo sapiens

<400> SEQUENCE: 25
aaggtgcctg ggggtcggtt                                           20

<210> SEQ ID NO 26
<211> LENGTH: 20
<212> TYPE: DNA
<213> ORGANISM: Homo sapiens

<400> SEQUENCE: 26
ggcctcgttt gcggtcagtt                                           20

<210> SEQ ID NO 27
<211> LENGTH: 20
<212> TYPE: DNA
```

<213> ORGANISM: Homo sapiens

<400> SEQUENCE: 27
agcagtgcgg ggctggatga                                          20

<210> SEQ ID NO 28
<211> LENGTH: 23
<212> TYPE: DNA
<213> ORGANISM: Homo sapiens

<400> SEQUENCE: 28
cctgtatgag tcctggtgtg ggt                                      23

<210> SEQ ID NO 29
<211> LENGTH: 20
<212> TYPE: DNA
<213> ORGANISM: Homo sapiens

<400> SEQUENCE: 29
agctgcagcc tgccgattcc                                          20

<210> SEQ ID NO 30
<211> LENGTH: 20
<212> TYPE: DNA
<213> ORGANISM: Homo sapiens

<400> SEQUENCE: 30
ttcctacaga ccccgccgtg                                          20

<210> SEQ ID NO 31
<211> LENGTH: 20
<212> TYPE: DNA
<213> ORGANISM: Homo sapiens

<400> SEQUENCE: 31
tgagggctgt gtctgttcgg                                          20

<210> SEQ ID NO 32
<211> LENGTH: 20
<212> TYPE: DNA
<213> ORGANISM: Homo sapiens

<400> SEQUENCE: 32
ttccgggtag agaaggaggg                                          20

<210> SEQ ID NO 33
<211> LENGTH: 20
<212> TYPE: DNA
<213> ORGANISM: Homo sapiens

<400> SEQUENCE: 33
atggtgatgt caggtgctgg                                          20

<210> SEQ ID NO 34
<211> LENGTH: 20
<212> TYPE: DNA
<213> ORGANISM: Homo sapiens

<400> SEQUENCE: 34
tggccgctgg tccacacctt                                          20

<210> SEQ ID NO 35
<211> LENGTH: 21

<212> TYPE: DNA
<213> ORGANISM: Homo sapiens

<400> SEQUENCE: 35
atcggtggag gcgaagatgc a                                              21

<210> SEQ ID NO 36
<211> LENGTH: 22
<212> TYPE: DNA
<213> ORGANISM: Homo sapiens

<400> SEQUENCE: 36
ggacctcaga accattcacg gt                                             22

<210> SEQ ID NO 37
<211> LENGTH: 21
<212> TYPE: DNA
<213> ORGANISM: Homo sapiens

<400> SEQUENCE: 37
gctccgagta ttgtgtgacc g                                              21

<210> SEQ ID NO 38
<211> LENGTH: 20
<212> TYPE: DNA
<213> ORGANISM: Homo sapiens

<400> SEQUENCE: 38
gtcttctggg tggcagtgat                                                20

<210> SEQ ID NO 39
<211> LENGTH: 18
<212> TYPE: DNA
<213> ORGANISM: Homo sapiens

<400> SEQUENCE: 39
acgccgagtt gagcaaga                                                  18

<210> SEQ ID NO 40
<211> LENGTH: 19
<212> TYPE: DNA
<213> ORGANISM: Homo sapiens

<400> SEQUENCE: 40
aggtacccaa ccctgagga                                                 19

<210> SEQ ID NO 41
<211> LENGTH: 19
<212> TYPE: DNA
<213> ORGANISM: Homo sapiens

<400> SEQUENCE: 41
ggtaccccga catccactt                                                 19

<210> SEQ ID NO 42
<211> LENGTH: 18
<212> TYPE: DNA
<213> ORGANISM: Homo sapiens

<400> SEQUENCE: 42
ggacctctgc ggaacaag                                                  18

<210> SEQ ID NO 43

```
<211> LENGTH: 19
<212> TYPE: DNA
<213> ORGANISM: Homo sapiens

<400> SEQUENCE: 43
gcaaccccgc cttactaat                                                    19

<210> SEQ ID NO 44
<211> LENGTH: 20
<212> TYPE: DNA
<213> ORGANISM: Homo sapiens

<400> SEQUENCE: 44
atgcaacctg accgagaagt                                                   20

<210> SEQ ID NO 45
<211> LENGTH: 21
<212> TYPE: DNA
<213> ORGANISM: Homo sapiens

<400> SEQUENCE: 45
catccacgag aattgtaccc g                                                 21

<210> SEQ ID NO 46
<211> LENGTH: 19
<212> TYPE: DNA
<213> ORGANISM: Homo sapiens

<400> SEQUENCE: 46
gcgggcagtg ccaagggcg                                                    19

<210> SEQ ID NO 47
<211> LENGTH: 19
<212> TYPE: DNA
<213> ORGANISM: Homo sapiens

<400> SEQUENCE: 47
gcggcttccg aaggaaatg                                                    19

<210> SEQ ID NO 48
<211> LENGTH: 18
<212> TYPE: DNA
<213> ORGANISM: Homo sapiens

<400> SEQUENCE: 48
agcaaaaccc ggaggagt                                                     18

<210> SEQ ID NO 49
<211> LENGTH: 20
<212> TYPE: DNA
<213> ORGANISM: Homo sapiens

<400> SEQUENCE: 49
aaggcctcag cacctaccta                                                   20

<210> SEQ ID NO 50
<211> LENGTH: 20
<212> TYPE: DNA
<213> ORGANISM: Homo sapiens

<400> SEQUENCE: 50
cgcccatgtg ggtcagtggg                                                   20
```

```
<210> SEQ ID NO 51
<211> LENGTH: 20
<212> TYPE: DNA
<213> ORGANISM: Homo sapiens

<400> SEQUENCE: 51
gccagtgtgc tgtcgttccc                                          20

<210> SEQ ID NO 52
<211> LENGTH: 20
<212> TYPE: DNA
<213> ORGANISM: Homo sapiens

<400> SEQUENCE: 52
gcctacaaat catccggcca                                          20

<210> SEQ ID NO 53
<211> LENGTH: 20
<212> TYPE: DNA
<213> ORGANISM: Homo sapiens

<400> SEQUENCE: 53
gactctgcac caagggactg                                          20

<210> SEQ ID NO 54
<211> LENGTH: 20
<212> TYPE: DNA
<213> ORGANISM: Homo sapiens

<400> SEQUENCE: 54
ccgaaagcgg agctcgaaac                                          20

<210> SEQ ID NO 55
<211> LENGTH: 20
<212> TYPE: DNA
<213> ORGANISM: Homo sapiens

<400> SEQUENCE: 55
gtgtaccaag tgtggagggg                                          20

<210> SEQ ID NO 56
<211> LENGTH: 20
<212> TYPE: DNA
<213> ORGANISM: Homo sapiens

<400> SEQUENCE: 56
catgactcca acttccacct                                          20

<210> SEQ ID NO 57
<211> LENGTH: 19
<212> TYPE: DNA
<213> ORGANISM: Homo sapiens

<400> SEQUENCE: 57
agccacatcg ctcagacac                                           19

<210> SEQ ID NO 58
<211> LENGTH: 18
<212> TYPE: DNA
<213> ORGANISM: Homo sapiens

<400> SEQUENCE: 58
tctgcctcct ccacgaag                                            18
```

```
<210> SEQ ID NO 59
<211> LENGTH: 23
<212> TYPE: DNA
<213> ORGANISM: Homo sapiens

<400> SEQUENCE: 59
gcaggtgagt tgtcagaata ggt                                            23

<210> SEQ ID NO 60
<211> LENGTH: 21
<212> TYPE: DNA
<213> ORGANISM: Homo sapiens

<400> SEQUENCE: 60
gcctgttctg gaaccatacc t                                              21

<210> SEQ ID NO 61
<211> LENGTH: 18
<212> TYPE: DNA
<213> ORGANISM: Homo sapiens

<400> SEQUENCE: 61
tgcagggaag ggtggata                                                  18

<210> SEQ ID NO 62
<211> LENGTH: 20
<212> TYPE: DNA
<213> ORGANISM: Homo sapiens

<400> SEQUENCE: 62
aactagtggc ggtcataggc                                                20

<210> SEQ ID NO 63
<211> LENGTH: 19
<212> TYPE: DNA
<213> ORGANISM: Homo sapiens

<400> SEQUENCE: 63
caggtcgcta ggggagatg                                                 19

<210> SEQ ID NO 64
<211> LENGTH: 21
<212> TYPE: DNA
<213> ORGANISM: Homo sapiens

<400> SEQUENCE: 64
agcaatccag tttaggggtg t                                              21

<210> SEQ ID NO 65
<211> LENGTH: 21
<212> TYPE: DNA
<213> ORGANISM: Homo sapiens

<400> SEQUENCE: 65
ccctcacctt caagcagctg c                                              21

<210> SEQ ID NO 66
<211> LENGTH: 20
<212> TYPE: DNA
<213> ORGANISM: Homo sapiens

<400> SEQUENCE: 66
caagtggccg ttcatcatgc                                                20
```

<210> SEQ ID NO 67
<211> LENGTH: 21
<212> TYPE: DNA
<213> ORGANISM: Homo sapiens

<400> SEQUENCE: 67
ccacatcggc ctgtgtatat c                                              21

<210> SEQ ID NO 68
<211> LENGTH: 20
<212> TYPE: DNA
<213> ORGANISM: Homo sapiens

<400> SEQUENCE: 68
attggaaggt tcccagtcgg                                                20

<210> SEQ ID NO 69
<211> LENGTH: 20
<212> TYPE: DNA
<213> ORGANISM: Homo sapiens

<400> SEQUENCE: 69
agccgggagc gctgtagtca                                                20

<210> SEQ ID NO 70
<211> LENGTH: 20
<212> TYPE: DNA
<213> ORGANISM: Homo sapiens

<400> SEQUENCE: 70
cttcctacag accccgccgt                                                20

<210> SEQ ID NO 71
<211> LENGTH: 20
<212> TYPE: DNA
<213> ORGANISM: Homo sapiens

<400> SEQUENCE: 71
ggttggaagc aaacgcacaa                                                20

<210> SEQ ID NO 72
<211> LENGTH: 20
<212> TYPE: DNA
<213> ORGANISM: Homo sapiens

<400> SEQUENCE: 72
cctcgagcgc gctaacatag                                                20

<210> SEQ ID NO 73
<211> LENGTH: 21
<212> TYPE: DNA
<213> ORGANISM: Homo sapiens

<400> SEQUENCE: 73
agtttccggg gttgaaactg g                                              21

<210> SEQ ID NO 74
<211> LENGTH: 20
<212> TYPE: DNA
<213> ORGANISM: Homo sapiens

<400> SEQUENCE: 74

-continued

```
aggtgcttca cccagttcag                                          20

<210> SEQ ID NO 75
<211> LENGTH: 20
<212> TYPE: DNA
<213> ORGANISM: Homo sapiens

<400> SEQUENCE: 75
acttgagctc gctgttctcg                                          20

<210> SEQ ID NO 76
<211> LENGTH: 19
<212> TYPE: DNA
<213> ORGANISM: Homo sapiens

<400> SEQUENCE: 76
gcccaatacg accaaatcc                                           19
```

RENAL PROGENITOR CELLS

REFERENCE TO SEQUENCE LISTING SUBMITTED ELECTRONICALLY VIA EFS-WEB

The content of the electronically submitted sequence listing (Name: 4866_0030003_Seqlisting_ST25.txt; Size: 11,687 Bytes; and Date of Creation: Jun. 11, 2021) is herein incorporated by reference in its entirety.

TECHNICAL FIELD

THIS INVENTION relates to kidney development. More particularly, this invention relates to an in vitro method of producing nephron progenitor cells and ureteric duct progenitor cells ultimately from human pluripotent stem cells.

BACKGROUND

With the prevalence of end stage renal disease rising 8% pa globally[1], there is an urgent need for renal regenerative strategies. The kidney is a mesodermal organ that differentiates from the intermediate mesoderm (IM) via the formation of a ureteric bud (UB) and the interaction between this bud and the adjacent IM-derived metanephric mesenchyme (MM)[2]. The nephrons arise from a nephron progenitor population derived from the MM[3]. The IM itself is derived from the posterior primitive streak[4]. While the developmental origin of the kidney is well understood[2], nephron formation in the human kidney is completed before birth[5]. Hence, there is no postnatal stem cell able to replace lost nephrons.

Human Pluripotent Stem cells have great potential for the generation of a cell-based treatment for kidney disease. However, the realisation of human pluripotent stem cells as a source of cells for clinical use and as a treatment, such as for kidney disease, has been hindered by the lack of understanding of how to produce the necessary cell types that give rise to nephrons and other structures of the kidney.

SUMMARY

The present inventors have successfully directed the differentiation of human pluripotential stem cells through posterior primitive streak and intermediate mesoderm (IM) under fully chemically defined monolayer culture conditions using growth factors used during normal embryogenesis. This differentiation protocol results in the synchronous induction of ureteric bud (UB) and metanephric mesenchyme (MM) that forms a self-organising structure, including nephron formation, in vitro. Such hESC-derived components show broad renal potential ex vivo, illustrating the potential for pluripotent stem cell-based renal regeneration.

Accordingly, one aspect of the invention provides a method of producing nephron progenitor cells and ureteric epithelial progenitor cells including the step of contacting intermediate mesoderm (IM) cells with: fibroblast growth factor 9 (FGF9) and/or fibroblast growth factor 20 (FGF20); and optionally, one or more agents selected from the group consisting of: bone morphogenic protein 7 (BMP7); heparin; a Wnt agonist; retinoic acid (RA), analog or agonist; and an RA antagonist; to thereby produce nephron progenitor cells and ureteric epithelial progenitor cells from the IM cells.

In one embodiment, the IM cells are derived or differentiated from posterior primitive streak cells.

In one embodiment, the posterior primitive streak cells are derived or differentiated from human pluripotent stem cells (hPSCs). Non-limiting examples of hPSCs include human embryonic stem cells (hESCs) and induced human pluripotent stem cells (iPSCs).

In a preferred form, this aspect provides a method that includes the sequential steps of:
(i) contacting hPSCs with one or more agents that facilitate differentiation of the hPSCs into posterior primitive streak cells;
(ii) contacting the posterior primitive streak cells with one or more agents that facilitate differentiation of the posterior primitive streak cells into IM cells; and
(iii) contacting IM cells with FGF9 alone or in combination with one or more of: BMP7; RA; an RA antagonist; a Wnt agonist; and/or FGF20; and heparin; to thereby produce nephron progenitor cells and ureteric epithelial progenitor cells from the IM cells.

The one or more agents at step (ii) preferably include FGF9. In one particular embodiment, FGF9 is present for at least part of, or entirely throughout, both steps (ii) and (iii). In a particularly preferred embodiment, a Wnt agonist such as CHIR99021 is present during step (i).

In one embodiment, the method further includes the step of identifying viable nephron progenitor cells and/or ureteric epithelial progenitor cells.

In certain embodiments, identification of viable nephron progenitor cells and/or ureteric epithelial progenitor cells includes measurement or detection of co-expression of a plurality of nucleic acids and/or proteins as markers for the viable nephron and/or ureteric epithelial progenitor cells.

In another aspect, the invention provides isolated, enriched or purified nephron and/or ureteric epithelial progenitor cells produced according to the method of the aforementioned aspect.

In yet another aspect, the invention provides a method of producing a kidney, or kidney cells or tissues, said method including the step of differentiating kidney, or kidney cells or tissues from the nephron progenitor cells and/or ureteric epithelial progenitor cells of the aforementioned aspect to thereby produce the kidney, or kidney cells or tissues.

In some embodiments, the nephron progenitor cells and/or ureteric epithelial progenitor cells may be used as a source for bioprinting or bio-engineering whole kidneys and kidney tissue for kidney transplant or treating chronic kidney disease.

In other embodiments, the nephron progenitor cells and/or ureteric epithelial progenitor cells may be used for the recellularisation of whole organ decellularised kidney to thereby create a reconstituted or replacement kidney.

In other embodiments, the nephron progenitor cells and/or ureteric epithelial progenitor cells may be used as a source for cellular therapy of kidney diseases and conditions.

In a further aspect, the invention provides a method of determining the nephrotoxicity of one or a plurality of compounds, said method including the step of contacting the one or plurality of compounds with the isolated or purified nephron progenitor cells and/or ureteric epithelial progenitor cells of the aforementioned aspect, or kidney cells or tissues differentiated or otherwise obtained therefrom, to thereby determine whether or not the one or plurality of compounds is nephrotoxic.

In one embodiment, this aspect provides bioprinting of the nephron progenitors and/or ureteric epithelial progenitors into kidney organoids for nephrotoxicity screening.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
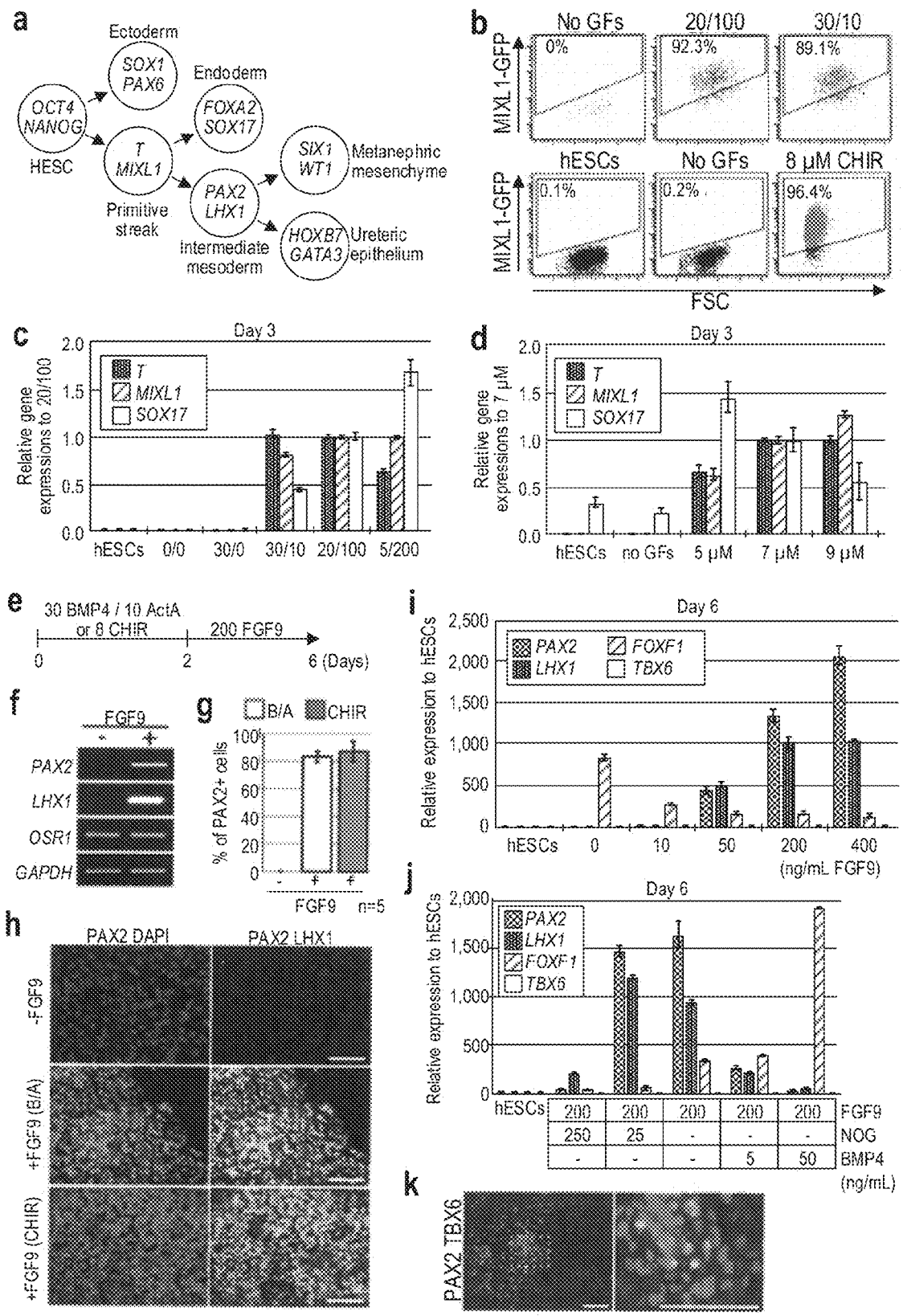
FIG. 1. Sequential differentiation of posterior primitive streak and intermediate mesoderm from human embryonic stem cells. a, Schematic of developmental stages from inner cell mass to renal lineages. Genes shown in each stage represent specific markers of that stage. b, FACS analysis (GFP and forward scatter (FSC)) showing the percentage of MIXL1-GFP positive posterior primitive streak cells induced with different ratios of BMP4/Activin A (ng/mL) or 8 µM of CHIR99021 after 3 days culture. hESC, starting cells; No GFs, 3 days culture with basal media. c, d, Relative expressions of SOX17, BRACHYURY (T) and MIXL1 at day 3 for each ratio of BMP4 and Activin A (ng/mL) assessed by qRT-PCR analysis (c). The same qRT-PCR analysis for different concentrations of CHIR99021 (d). Error bars are s.d. (n=3 experiments). e, Schematic representation of the differentiation protocol used from hESC to IM. f, RT-PCR at day 6 showing the expression of markers of IM (PAX2, LHX1, OSR1) in the presence or absence of 200 ng/ml FGF9 from day 2 to 6. g, Quantitation of the percentage of cells positive for PAX2 protein at day 6 in the presence or absence of 200 ng/ml FGF9 from day 2 to 6. Both differentiation protocols via BMP4/Activin A (B/A) and CHIR99021 (CHIR) exceeded 80% induction efficiency. Error bars are s.d. (n=5 fields in total from 3 experiments). h, The presence and co-expression of PAX2 (red) and LHX1 (green) proteins at day 6 via posterior primitive streak induction using either BMP4/Activin A (B/A) or CHIR99021 (CHIR). (scale=100 µm) i, qRT-PCR showing the expression of markers of IM (PAX2, LHX1), PM (TBX6) and LPM (FOXF1) at day 6 across a concentration gradient of FGF9 from day 2 to 6. Error bars are s.d. (n=3 experiments). j, qRT-PCR showing the expression change of mesoderm markers at day 6 in the presence of FGF9 together with NOG or BMP4 from day 2 to 6. Error bars are s.d. (n=3 experiments). k, IF at day 6 showing a major IM population marked by PAX2 (red) and a non-overlapping PM marked by TBX6 (green). (scale=100 µm).

The invention is at least partly predicated on the identification of specific in vitro culture conditions that are tailored to promote the synchronous, simultaneous differentiation of nephron progenitor cells and ureteric epithelial progenitor from intermediate mesoderm (IM). More specifically, FGF9 plus heparin alone, or in combination with one or more agents including bone morphogenic protein 7 (BMP7), retinoic acid (RA), an RA antagonist; a Wnt agonist; and/or FGF20 plus heparin, is capable of facilitating differentiation of intermediate mesoderm into nephron progenitor cells and ureteric epithelial progenitors. Further to this, the in vitro culture method provides a system for differentiating human embryonic stem cells through posterior primitive streak, IM and metanephric mesenchymal stages to produce nephron progenitor cells and ureteric epithelial progenitor cells. Advantageously, the presence or absence of certain molecules such as RA, RA antagonist and/or Wnt agonist can be manipulated to preferentially promote the production of nephron progenitor cells versus ureteric epithelial progenitors, or vice versa.

The nephron progenitor cells and ureteric epithelial progenitor cells are simultaneously induced, direct the differentiation of each other in vivo and are capable of developing into distinct tubular epithelial structures, including ureteric tree and nephron progenitor mesenchyme, during which the epithelial structures substitute for the ureteric tip to maintain the nephron progenitor cells. It is therefore proposed that the hESC-derived ureteric epithelium and/or nephron progenitor cells produced according to the invention may be directed to differentiate into renal cells from both the ureteric and mesenchymal compartments. Furthermore, the capacity of these cells to 'self-organise' may therefore be exploited to facilitate kidney repair, such as by way of kidney bioengineering. The nephron progenitor cells, nephrons derived therefrom or kidney organoids "self organized" as described above, may also be suited to nephrotoxicity testing, which has been hampered by a previous inability to produce cells suitable for testing.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described.

As used herein, except where the context requires otherwise, the term "comprise" and variations of the term, such as "comprising", "comprises" and "comprised", are not intended to exclude further additives, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

For the purposes of this invention, by "isolated" is meant material that has been removed from its natural state or otherwise been subjected to human manipulation. Isolated material (e.g., cells) may be substantially or essentially free from components that normally accompany it in its natural state, or may be manipulated so as to be in an artificial state together with components that normally accompany it in its natural state.

By "enriched" or "purified" is meant having a higher incidence, representation or frequency in a particular state (e.g an enriched or purified state) compared to a previous state prior to enrichment or purification.

The terms "differentiate", "differentiating" and "differentiated", relate to progression of a cell from an earlier or initial stage of a developmental pathway to a later or more mature stage of the developmental pathway. It will be appreciated that in this context "differentiated" does not mean or imply that the cell is fully differentiated and has lost pluropotentiality or capacity to further progress along the developmental pathway or along other developmental pathways. Differentiation may be accompanied by cell division.

A "progenitor cell" is a cell which is capable of differentiating along one or a plurality of developmental pathways, with or without self-renewal. Typically, progenitor cells are unipotent or oligopotent and are capable of at least limited self-renewal.

As will be well understood in the art, the stage or state of differentiation of a cell may be characterized by the expression and/or non-expression of one of a plurality of markers. In this context, by "markers" is meant nucleic acids or proteins that are encoded by the genome of a cell, cell population, lineage, compartment or subset, whose expression or pattern of expression changes throughout development. Nucleic acid marker expression may be detected or measured by any technique known in the art including nucleic acid sequence amplification (e.g. polymerase chain reaction) and nucleic acid hybridization (e.g. microarrays, Northern hybridization, in situ hybridization), although without limitation thereto. Protein marker expression may be detected or measured by any technique known in the art including flow cytometry, immunohistochemistry, immunoblotting, protein arrays, protein profiling (e.g 2D gel electrophoresis), although without limitation thereto.

One aspect of the invention provides a method of producing nephron progenitor cells and ureteric epithelial progenitor cells including the step of contacting intermediate mesoderm (IM) cells with: BMP7; retinoic acid (RA); RA antagonist; a Wnt agonist; fibroblast growth factor 9 (FGF9) and/or FGF20; and heparin; to thereby produce nephron progenitor cells and ureteric epithelial progenitor cells from the IM cells.

Reference herein to "retinoic acid" or "RA" includes all forms of retinoic acid (e.g including all trans RA and 9-cis RA), analogs and/or retinoic acid receptor (RAR) agonists that have a similar biological activity to RA. Various different RA analogs and RAR agonists (including agonists non-selective and selective for RARα, β or γ) are commercially available such as from R & D Systems and Tocris Bioscience.

Specific reference to an "RA antagonist" includes retinoic acid receptor (RAR) antagonists and any other molecule(s) that inhibit, block or prevent RA signalling via the RAR. Non-limiting examples of RAR antagonists include AGN193109, LE 135, ER 50891, BMS 493, BMS 453 and MM 11253, although without limitation thereto. This definition does not exclude the possibility that the RA antagonist also or alternatively mimics a block in signalling via RAR from binding of another ligand.

As used herein a "Wnt agonist" is a molecule that inhibits GSK3 (e.g GSK3-β) in the context of the canonical Wnt signalling pathway, but preferably not in the context of other non-canonical, Wnt signalling pathways. Non-limiting examples of Wnt agonists include CHIR99021, LiCl SB-216763, CAS 853220-52-7 and other Wnt agonists that are commercially available from sources such as Santa Cruz Biotechnology and R & D Systems. This definition should not be read as absolutely excluding the possibility that the Wnt agonist mimics one or more other inhibitors of GSK3β activity.

It will also be appreciated that fibroblast growth factors such as FGF9 and FGF20 may be interchangeable, although FGF9 is preferred. Heparin is typically included to promote or enhance the biological activity of fibroblast growth factors such as FGF2, FGF9 and/or FGF20.

The preferred concentrations of each of FGF9, BMP7, retinoic acid (RA); RA antagonist; Wnt agonist; FGF20 and heparin will be described in more detail hereinafter. Reference will also be made to controlling or manipulating the presence or absence of certain molecules such as RA agonist or analog, RA antagonist and/or Wnt agonist to preferentially promote the production of nephron progenitor cells versus ureteric epithelial progenitors, or vice versa.

As used herein "nephron progenitor cells" are progenitor cells derived from metanephric mesenchyme that can differentiate into all nephron segments (other than collecting duct) via an initial mesenchyme to epithelial transition, which include nephron epithelia such as connecting segment, distal convoluted tubule (DCT) cells, distal straight tubule (DST) cells, proximal straight tubule (PST) segments 1 and 2, PST cells, podocytes, glomerular endothelial cells, ascending Loop of Henle and/or descending Loop of Henle, although without limitation thereto. Nephron progenitor cells are also capable of self-renewal.

Non-limiting examples of markers characteristic or representative of metanephric mesenchyme include WT1, SIX1, SIX2, SALL1, GDNF and/or HOXD11, although without limitation thereto. Non-limiting examples of markers characteristic or representative of nephron progenitor cells include WT1, SIX1, SIX2, CITED1, PAX2, GDNF, SALL1, OSR1 and HOXD11, although without limitation thereto.

By "ureteric epithelial progenitor cell" is meant an epithelial progenitor cell derived, obtainable or originating from mesonephric duct or its derivative ureteric bud that can develop into kidney tissues and/or structures such as the collecting duct.

Non-limiting examples of characteristic or representative markers of ureteric epithelial progenitor cells include HOXB7, cRET, GATA3, CALB1, E-CADHERIN and PAX2, although without limitation thereto.

As hereinbefore described, the nephron progenitor cells and ureteric epithelial progenitor cells are differentiated from intermediate mesoderm (IM) cells is the presence of FGF9 alone or in combination with one or more agents that include BMP7, retinoic acid (RA), agonist or analog, an RA antagonist such as AGN193109 and/or FGF20 and preferably heparin.

By "intermediate mesoderm (IM)" cells is meant embryonic mesodermal cells that arise from posterior primitive streak and can ultimately develop into the urogenital system, inclusive of the ureter and kidney and other tissues such as gonad. Non-limiting examples of markers characteristic or representative of intermediate mesoderm include PAX2, OSR1 and/or LHX1.

It will also be appreciated that production of IM cells is not meant to imply that the IM cells are a pure or homogeneous population of IM cells without other cell types being present. Accordingly, reference to "IM cells" or a "population of IM cells" means that the cells or cell population comprise(s) IM cells.

Suitably, according to the invention IM cells are produced by contacting posterior primitive streak cells with one or more agents that facilitate differentiation of the posterior primitive streak cells into IM cells, as will be described in more detail hereinafter.

Preferably, the IM cells are produced by contacting posterior primitive streak cells with one or more agents that facilitate differentiation of the posterior primitive streak cells into IM cells Typically, the one or more agents include fibroblast growth factor 9 (FGF9) and, optionally, an RA antagonist such as AGN193109 and/or one or more other FGFs such as FGF 2 and/or FGF20.

By "posterior primitive streak (PPS)" cells is meant cells obtainable from, or cells functionally and/or phenotypically corresponding to, cells of the posterior end of a primitive streak structure that forms in the blastula during the early stages of mammalian embryonic development. The posterior primitive streak establishes bilateral symmetry, determines the site of gastrulation and initiates germ layer formation. Typically, posterior primitive streak is the progenitor of mesoderm (i.e presumptive mesoderm) and anterior primitive streak is the progenitor of endoderm (i.e presumptive endoderm). Non-limiting examples of markers characteristic or representative of posterior primitive streak include Brachyury (T). A non-limiting example of a marker characteristic or representative of anterior primitive streak is SOX17. MIXL1 may be expressed by both posterior and anterior primitive streak.

It will also be appreciated that production of posterior primitive streak cells is not meant to imply that the posterior primitive streak cells are a pure or homogeneous population of posterior primitive streak cells without other cell types being present. Accordingly, reference to "posterior primitive streak cells" or a "population of posterior primitive streak cells" means that the cells or cell population comprise(s) posterior primitive streak cells.

Suitably, according to the invention posterior primitive streak cells are produced by contacting hPSC cells with one or more agents that facilitate differentiation of the hPSC cells into posterior primitive streak cells, as will be described in more detail hereinafter.

Typically, the one or more agents include bone morphogenic protein 4 (BMP4), Activin A and/or a Wnt agonist such as CHIR99021.

The terms "human pluripotent stem cell" and "hPSC" refer to cells derived, obtainable or originating from human tissue that display pluripotency. The hPSC may be a human embryonic stem cell or a human induced pluripotent stem cell.

Human pluripotent stem cells may be derived from inner cell mass or reprogrammed using Yamanaka factors from many fetal or adult somatic cell types. The generation of hPSCs may be possible using somatic cell nuclear transfer.

The terms "human embryonic stem cell", "hES cell" and "hESC" refer to cells derived, obtainable or originating from human embryos or blastocysts, which are self-renewing and pluri- or toti-potent, having the ability to yield all of the cell types present in a mature animal. Human embryonic stem cells (hESCs) can be isolated, for example, from human blastocysts obtained from human in vivo preimplantation embryos, in vitro fertilized embryos, or one-cell human embryos expanded to the blastocyst stage.

The terms "induced pluripotent stem cell" and "iPSC" refer to cells derivable, obtainable or originating from human adult somatic cells of any type reprogrammed to a pluripotent state through the expression of exogenous genes, such as transcription factors, including a preferred combination of OCT4, SOX2, KLF4 and c-MYC. hiPSC show levels of pluripotency equivalent to hESC but can be derived from a patient for autologous therapy with or without concurrent gene correction prior to differentiation and cell delivery.

More generally, the method disclosed herein could be applied to any pluripotent stem cell derived from any patient or a hPSC subsequently modified to generate a mutant model using gene-editing or a mutant hPSC corrected using gene-editing. Gene-editing could be by way of CRISPR, TALEN or ZF nuclease technologies.

It will be appreciated from the foregoing, that a preferred broad form the invention provides a method that includes the sequential steps of:
 (i) contacting hPSCs with one or more agents that facilitate differentiation of the hPSCs into posterior primitive streak cells;
 (ii) contacting posterior primitive streak cells with one or more agents that facilitate differentiation of the posterior primitive streak cells into intermediate mesoderm cells; and
 (iii) contacting intermediate mesoderm cells with FGF9 and, optionally, one or more of: BMP7; retinoic acid; an RA antagonist such as AGN193109; a Wnt agonist such as CHIR99021; FGF20; and heparin; to thereby produce metanephric mesenchyme cells and ureteric epithelial progenitor cells from the intermediate mesoderm cells.

These sequential steps will be described hereinafter as follows.

(i) Differentiating hPSCs into Posterior Primitive Streak

As will be appreciated from the foregoing, hPSCs are contacted with BMP4, Activin A and/or CHIR99021 in a suitable culture medium in the absence of serum, such as APEL differentiation medium (Ng et al., 2008, Nat. Protoc. 3: 768), although without limitation thereto, to thereby produce posterior primitive streak cells that suitably comprise posterior primitive streak cells. The hPSCs may be hESCs or iPSCs.

Suitably, BMP4 is at a concentration of about 5-40 ng/mL and Activin A is at a concentration of about 3-40 ng/mL. In one embodiment the concentration of BMP4 is about 20-35 ng/mL, or more preferably about 30 ng/mL. In one embodiment, the concentration of Activin A is about 5-30 ng/mL or more preferably 10 ng/mL. Suitably, an optimal relative activity ratio is in the range of 3:1 to 1:6 BMP4 to Activin A. Preferably, an optimal relative activity ratio is in the range of 3:1 to 1:1 BMP4 to Activin A.

In some embodiments, a Wnt agonist such as CHIR99021 may be at a concentration in the range of about 0.5 to 50 μM, preferably about 4-30 μM, more preferably about 5-20 μM or advantageously about 8 μM. In certain embodiments, CHIR99021 is present alone, in the absence of BMP4 and Activin A.

The population of stem cells may be cultured in the medium with BMP4, Activin A and/or a Wnt agonist such as CHIR99021 for 36-120 hours.

In some non-limiting embodiments, cells may be contacted for longer periods with BMP4, Activin A and/or CHIR99021 than is required for hESCs. By way of example, cells such as iPSCs may be contacted with BMP4, Activin A and/or CHIR99021 for up to 96-120 hrs.

The culture medium may be changed every 24-48 hrs.

Although not wishing to be bound by theory, contacting hPSCs with BMP4, Activin A and/or a Wnt agonist such as CHIR99021 as disclosed herein results in formation of primitive streak (PS) including posterior primitive streak. This is an initial step towards the generation of mesodermal and endodermal tissue. Typically, differentiation of hPSCs is toward a mixed population of cells that comprises cells expressing markers characteristic of posterior primitive streak (i.e. presumptive mesoderm) and cells expressing markers characteristic of anterior primitive streak (i.e. presumptive endoderm).

Non-limiting examples of markers characteristic of posterior primitive streak (presumptive mesoderm) include Brachyury (T).

A non-limiting example of a marker characteristic of anterior primitive streak (presumptive endoderm) is SOX17.

iii) Differentiation of Posterior Primitive Streak Cells into Intermediate Mesoderm (IM)

Suitably, posterior primitive streak cells, or a mixed primitive streak population comprising posterior primitive streak cells, are contacted with one or more fibroblast growth factors (FGFs) that at least includes FGF9 and, optionally, FGF2 and/or FGF20 and/or a retinoic acid (RA) antagonist in a suitable culture medium in the absence of serum, such as APEL differentiation medium.

Typically, the retinoic acid signalling antagonist is a retinoic acid receptor (RAR) inhibitor or antagonist such as AGN193109.

Suitably, FGF2, FGF9 and/or FGF20 are at a concentration of about 100 to 400 ng/mL. In a preferred embodiment, FGF2, FGF9 and/or FGF20 are at a concentration of about 150 to 300 ng/ML or advantageously about 200 ng/mL. In one embodiment, the concentration of the RA antagonist (e.g. AGN193109) is about 0.1-10 µM or more preferably 0.5-5 µM.

The cells are contacted with FGF9, alone or together with FGF2 and/or FGF20 and/or RA antagonist (e.g. AGN193109) for at least about 96 hours but not more than about 190-200 hours. Preferably, the cells are contacted with FGF9 alone or with FGF2 and/or FGF20 and/or RA antagonist (e.g AGN193109) for about 96 hours.

The culture medium may be changed every 40-48 hrs.

In one embodiment, contacting the posterior primitive streak cells (which typically express markers characteristic of posterior primitive streak (presumptive mesoderm) and anterior primitive streak (presumptive endoderm)) with FGF9 alone or together with FGF2 and/or FGF20 results in differentiation of the cells toward a population of cells expressing markers characteristic of intermediate mesoderm (IM). Non-limiting examples of markers characteristic of intermediate mesoderm include PAX2, LHX1 and OSR1.

(iii) Differentiation of Intermediate Mesoderm (IM) into Nephron Progenitors and Ureteric Epithelial Progenitors Suitably, following contacting posterior primitive streak cells with FGF2, FGF9 and/or FGF20, resultant IM cells are contacted with FGF9 alone or in combination with one or more of BMP7, RA, RA antagonist, FGF20, a Wnt agonist and/or heparin in a suitable culture medium in the absence of serum, such as APEL differentiation medium.

Suitably, FGF9 is at a concentration of about 20 ng to 1 µg/mL. In a preferred embodiment, FGF9 is at a concentration of about 50-500 ng/mL, more preferably about 100-300 ng/mL or advantageously about 200 ng/mL. Typically, heparin is included at a concentration of about 0.1-10 µg/mL, preferably about 0.3-5 µg/mL, 0.5-2 µg/mL or advantageously about 1 µg/mL.

In an embodiment, FGF20 is at a concentration of about 20 ng to 1 µg/mL. In a preferred embodiment, FGF 20 is at a concentration of about 50-500 ng/mL, more preferably about 100-300 ng/mL or advantageously about 200 ng/mL.

It will be appreciated that FGF20 may replace or supplement FGF9, as these agents have similar biological activities.

In an embodiment, BMP7 is at a concentration of about 25 to 75 ng/mL. In a preferred embodiment, BMP7 is at a concentration of about 35-60 ng/mL, 45-55 ng/mL or advantageously about 50 ng/mL.

In an embodiment, RA is at a concentration of about 10 pM to 1 µM. In a preferred embodiment, RA is at a concentration of about 30 pM to 0.5 µM, more preferably about 50 pM to 0.2 µM or advantageously about 0.1 µM. Although not binding on the present invention, preliminary data suggest that higher concentrations of RA promote a relative increase in the proportion of ureteric epithelial progenitor cells and that lower concentrations of RA promote a relative decrease in the proportion of ureteric epithelial progenitor cells.

In an embodiment, an RA antagonist such as AGN193109 is at a concentration of about 50 pM to 10 µM. In a preferred embodiment, AGN193109 is at a concentration of about 0.01 µM to 5 µM, more preferably about 0.1 µM to 5 µM or advantageously about 1 µM. Although not binding on the present invention, preliminary data suggest that higher concentrations of AGN193109 promote a relative increase in the proportion of metanephric mesenchyme cells.

In an embodiment, a Wnt agonist such as CHIR99021 is present at a concentration in the range of about 0.1 µM to 10 µM, preferably about 0.2 µM to 5 µM or more preferably at about 1-2 µM.

Although not binding on the present invention, preliminary data suggest that the Wnt agonist promotes a relative increase in the production of nephron progenitor cells from the IM cells. Preferably, cells are contacted with FGF9 alone or together with one or more of BMP7, RA, Wnt agonist, RA antagonist and/or FGF20 plus heparin for at least 72 hours but not more than 360 hours. Preferably, the cells are contacted for about 160-220 hrs or more preferably for about 190-200 hours.

The culture medium may be changed every 48-72 hrs.

Typically, contacting intermediate mesoderm cells with FGF9 alone or together with one or more of BMP7, RA, an RA antagonist; a Wnt agonist and/or FGF20 and preferably heparin, as disclosed herein, differentiates the intermediate mesoderm cells into cells of metanephric mesenchyme and ureteric epithelium cell lineages. The metanephric mesenchyme lineage includes nephron progenitor cells that are optimally produced after about 72 hrs of culture in FGF9 and heparin. It is also proposed that the presence, absence and/or concentration of RA analog or agonist and/or RA antagonist may be chosen to manipulate the relative amount of ureteric epithelium that is produced by the method, compared to metanephric mesenchyme that is produced by the method. As described previously, RA promotes the formation of ureteric epithelium at the expense of metanephric mesenchyme, whereas an RA antagonist such as AGN193109 promotes the formation of metanephric mesenchyme at the expense of ureteric epithelium. A Wnt agonist such as CHIR99021 may also promotes the survival and/or formation of metanephric mesenchyme at the expense of ureteric epithelium.

Non-limiting examples of markers characteristic or representative of cells of the metanephric mesenchyme lineage or cells thereof include WT1, SIX1, SIX2, SALL1, GDNF and/or HOXD11, although without limitation thereto.

Non-limiting examples of markers characteristic or representative of nephron progenitor cells include WT1, SIX2, CITED1, PAX2, GDNF, SALL1 and HOXD11, although without limitation thereto.

Non-limiting examples of markers characteristic or representative of cells of the ureteric epithelial lineage include HOXB7, GATA3, CALB1, E-CADHERIN, PAX2 and/or cRET, although without limitation thereto.

Nephron progenitor cells are likely to be maximally generated 11-15 days, or advantageously 14 days (range of day 11 to 15) after commencement of the method from the start of hPSC cell culture, based upon the co-expression of WT1, SIX2, CITED1, PAX2, GDNF, SALL1 and HOXD11.

Ureteric epithelial progenitor cells may be maximally generated after at least 10 days, or advantageously 14 days after commencement of the method from the start of hPSC culture, based upon the co-expression of HOXB7, cRET, E-CADHERIN and PAX2.

In a preferred form of the method, FGF9 is present for at least part of, or entirely throughout, both steps (ii) and (iii) described herein. More preferably, a Wnt agonist such as CHIR99021 is present for at least part of step (i) described herein.

A particularly preferred method therefor includes the sequential steps of:
 (a) contacting human pluripotent stem (hPCS) cells with CHIR99021 to facilitate differentiation of the hPSC cells into posterior primitive streak cells;
 (b) contacting the posterior primitive streak cells with FGF9, alone or together with an RA antagonist such as AGN193109, to facilitate differentiation of the posterior primitive streak cells into IM cells; and
 (c) contacting the IM cells with FGF9 and heparin, alone or together with an RA antagonist such as AGN193109, to thereby produce nephron progenitor cells and ureteric epithelial progenitor cells from the IM cells.

According to this preferred form, it is possible to facilitate kidney differentiation from an initial population of hES cells in a total culture period of about 18-20 days.

In light of the foregoing, reference to protein agents such as BMP4, BMP7, Activin A, FGF2, FGF9 and FGF20 should be understood as encompassing native or recombinant or chemical synthetic proteins of any mammalian origin, inclusive of human, mouse and rat, although without limitation thereto. Furthermore, these proteins may include chemical modifications, glycosylation, lipidation, labels such as biotin and additional amino acid sequences such as epitope tags or fusion partners as are well known in the art. Typically, the aforementioned proteins may be obtained commercially and/or prepared as recombinant or chemical synthetic proteins by routine laboratory or manufacturing procedures.

In another aspect, the invention provides isolated or purified nephron progenitor cells and/or ureteric epithelial progenitor cells produced according to the method disclosed herein.

It will be appreciated that nephron progenitor cells and/or ureteric epithelial progenitor cells may be obtained after an appropriate period of culture as hereinbefore described and in some optional embodiments may be further enriched or purified according to co-expression of surface markers. Cell enrichment or purification may be by any technique or process known in the art inclusive of flow cytometric cell sorting (e.g. FACS), positive or negative cell selection by magnetic immunobeads (e.g Dynabeads™), panning, density separation, complement mediated lysis or the like, although without limitation thereto.

Kidney Regeneration and Transplantation

Chronic kidney disease is a serious medical condition that affects 31 million Americans and 1.7 million Australians each year. Patients can lose 90% of their kidney function before they become symptomatic, resulting in kidney failure and dialysis or a kidney transplant. Medicare expenditure in the U.S. for end-stage renal disease was estimated at $28 billion in 2010.

Accordingly, an aspect of the invention provides a method of producing a kidney, or kidney cells or tissues, said method including the step of differentiating the kidney, or the kidney cells or tissues from the isolated or purified nephron and/or ureteric epithelial progenitor cells to thereby produce the kidney, or kidney cells or tissues.

The invention provides a method for producing cells of the ureteric epithelium and metanephric mesenchyme lineages or compartments. Preferably, these cells are simultaneously induced and direct the differentiation of each other in vivo. These cells are capable of developing into distinct tubular epithelial structures, including ureteric tree and nephron progenitor mesenchyme. It is therefore proposed that the hPSC cell-derived ureteric epithelium and/or nephron progenitor cells produced according to the invention may be directed to differentiate into renal cells from both the ureteric and mesenteric mesenchymal compartments.

Under appropriate conditions, the nephron progenitor cells may be capable of differentiating into any nephron segment (other than collecting duct) including nephron epithelia such as connecting segment, distal convoluted tubule (DCT) cells, distal straight tubule (DST) cells, proximal straight tubule (PST) segments 1 and 2, PST cells, podocytes, glomerular endothelial cells, ascending loop of Henle and/or descending loop of Henle, although without limitation thereto.

Furthermore, the capacity of these cells to 'self-organise' may therefore be exploited to facilitate kidney repair, such as by way of kidney tissue or organ bioengineering.

It will be appreciated that one embodiment of the method of this aspect may include adoptively transferring or transplanting the isolated or purified nephron and/or ureteric epithelial progenitor cells into a human to thereby produce the kidney, or kidney cells or tissues.

According to this embodiment. differentiation of the isolated or purified nephron and/or ureteric epithelial progenitor cells into the kidney or kidney cells or tissues occurs in vivo Another embodiment of the method of this aspect may include at least partly differentiating the isolated or purified nephron and/or ureteric epithelial progenitor cells in vitro into kidney, or kidney cells or tissues, or progenitors of these. Suitably, the at least partly in vitro differentiated cells kidney, or kidney cells or tissues, or progenitors thereof, are adoptively transferred or transplanted into a human.

According to either or both embodiments, the kidney, kidney cells or tissues may facilitate or contribute to regeneration of the kidney, cells or tissues thereof.

One embodiment provides use of the isolated nephron progenitors and/or ureteric epithelial progenitors to produce an engineered or artificial kidney. For example, isolated nephron progenitors and/or ureteric epithelial progenitors may be incorporated within a scaffold, such as a decellularised human kidney, polyester fleece or biodegradable polymer scaffold, to thereby produce a regenerated renal tubule structure.

Another embodiment of the invention provides use of kidney cells or tissues differentiated from the isolated nephron progenitors and/or ureteric epithelial progenitors in devices for assisting or facilitating renal dialysis. For example, bioartificial kidneys may be made by seeding kidney cells, or their progenitors into reactors to produce a 'renal assistance device' for use in parallel with dialysis.

Also contemplated are "bioprinted" kidneys or other nephron-containing organs, organoids or organ-like structures using kidney cells or tissues differentiated or otherwise obtained from the isolated nephron progenitors and/or ureteric epithelial progenitors described herein.

By way of example only, Organovo partnered with Invetech have developed an organ printing machine which uses a hydrogel scaffold to place human cells in a desired orientation to recreate human organs. Kidney cells or tissues differentiated or otherwise obtained from the isolated nephron progenitors and/or ureteric epithelial progenitors described herein may be used with machines, such as the Organovo machine referred to above, to develop a "bioprinted" human kidney organoid or kidney.

It will also be appreciated that the directed differentiation of isolated nephron progenitors and/or ureteric epithelial progenitors described herein may provide potential sources of purified, differentiated renal cell subtypes for cellular therapy.

For example, the isolated nephron progenitors and/or ureteric epithelial progenitors described herein may be useful for generating renal cells or tissues after gene correction in certain genetically-inherited renal conditions. For example, correction of single gene renal disorders, including Alport syndrome (COL4A3 mutation) and the polycystic kidney diseases (PKD1, PKD2 and others), may be assisted or facilitated by regeneration of renal tissue from the isolated nephron progenitors and/or ureteric epithelial progenitors described herein after gene correction.

In a particular embodiment, iPSC lines derived, obtained or originating from a patient with genetic renal disease may be used for repair of genetic mutation(s) in vitro. Such cells could be used according to the method of the invention and then administered to the patent for autologous cellular therapy.

Nephrotoxicity Screening

It will also be appreciated that the directed differentiation of isolated nephron progenitors and/or ureteric epithelial progenitors described herein may provide potential sources of purified, differentiated renal cell, renal organoids or renal tissue subtypes for nephrotoxicity screening.

The development of interventions aimed at preventing disease, including drug and cellular-based therapies, is made difficult by the lack of availability of primary human kidney cells for in vitro drug testing.

Accordingly, another aspect of the invention provides a method of determining the nephrotoxicity of one or a plurality of compounds, said method including the step of contacting the one or plurality of compounds with the nephron progenitor cells and/or ureteric epithelial progenitor cells described herein, either as an organoid or after isolation and purification, or kidney cells or tissues differentiated or otherwise obtained therefrom, to thereby determine whether or not the one or plurality of compounds is nephrotoxic.

Preferably, the method is performed using organoids or from isolated or purified nephron progenitor cells, or kidney cells or tissues derived from the nephron progenitor cells.

Many useful drugs have nephrotoxic side effects, such as by direct tubular effects (e.g aminoglycoside antibiotics, cisplatin, radiocontrast media, NSAIDs, ACE inhibitors), interstitial nephritis (e.g lactam antibiotics, lithium, CsA, anti-epileptic drugs such as phenytoin) or glomerulonephritis, for example. It may therefore be advantageous to test new or existing drugs using defined, specific kidney cells and tissue types differentiated or otherwise obtained from the isolated or purified nephron progenitor cells described herein. The hereinbefore described "bioprinted" kidney or bioprinted kidney organoid may also be applicable to nephrotoxicity screening.

Nephrotoxicity may be assessed or measured by any appropriate test for renal cell function in vitro, including decreased creatinine clearance or biomarker expression such as by the Human Nephrotoxicity $RT^2$ Profiler™ PCR Array from Qiagen or the High Content Analysis (HCA) Multiplexed Nephrotoxicity Assay from Eurofins, although without limitation thereto.

So that the invention may be readily understood and put into practical effect, reference is made to the following non-limiting Examples.

Examples

Materials and Methods
hESC Culture and Differentiation

HES3 (MIXL1$^{GFP/wt}$) cells were routinely cultured on irradiated MEF feeder cells in F12/DMEM (Life Technologies) supplemented with 20% KnockOut serum replacement (Life Technologies), 100 μM MEM NEAA (Life Technologies), 110 μM 2-mercaptoethanol (Life Technologies), 1× penicillin/streptomycin (Life Technologies), 1×Glutamax (Life Technologies) and 10 ng/mL bFGF (R&D systems). The day before starting differentiation, cells were plated at 12,000-15,000 cells/cm$^2$ on a Matrigel coated 96-well plate. After overnight culture, cells were exposed to 30 ng/mL BMP4 (R&D systems) and 10 ng/mL Activin A (R&D systems) or 8 μM CHIR99021 in a previously established serum free media APEL for 2-3 days, then 200 ng/mL FGF9 and 1 μg/mL Heparin in APEL media for 4 days to induce IM cells. Subsequently cells were exposed to 200 ng/mL FGF9, 50 ng/mL BMP7, 0.1 μM RA and 1 μg/mL Heparin for 4-11 days in case of BMP4/Activin A induction. In case of CHIR99021 induction, cells were exposed to 200 ng/mL FGF9 and 1 μg/mL Heparin for 6 days then cultured in APEL basal media for another 6 days. Media was changed every 2 days.

Fluorescein-Activated Cell Sorting

Cell suspension was prepared from undifferentiated or differentiated hESCs. hESCs were harvested with TripLE Select (Life Technologies) at 37° C. for 5 min and dissociated using fine-tipped pipettes. After the cells had been filtered through a 40 μm nylon mesh, they were resuspended in PBS containing 0.5% FCS and 1 mM EDTA at a final density of 2×10$^6$ cells/ml. Propidium Iodide (Sigma) was added at a final concentration of 50 mg/ml to label the dead cells. FACS analyses were done with the FACS Aria (Becton Dickinson). Dead cells were excluded from the plots based on propidium iodide. All FACS analyses were successfully repeated more than three times and representative results were shown.

Immunocytochemistry

Cells were fixed with 4% Paraformaldehyde in PBS for 10 min at 4° C. followed by a wash with PBS. Then cells were blocked with 1% BSA, 0.2% milk, 0.3% Triton X/PBS for 1 hr at RT and incubated with primary antibodies overnight at 4° C. Secondary antibodies were incubated for 1 hr at RT. The following antibodies and dilutions were used: rabbit anti-PAX2 (1:200, #71-6000, Zymed Laboratories Inc.), goat anti-OSR1 (1:75, #sc-67723, Santa Cruz Biotechnology), goat anti-LHX1 (1:75, #sc-19341, Santa Cruz Biotechnology), mouse anti-TBX6 (1:200, AF4744, R&D systems), goat anti-SOX17 (1:200, #AF1924, R&D systems), rabbit anti-SIX2 (1:200, #11562-1-AP, Proteintech), mouse anti-ECAD (1:200, #610181, BD Biosciences), rabbit anti- WT1 (1:100, #sc-192, Santa Cruz Biotechnology), mouse anti-HOXD11 (1:200, #SAB1403944, Sigma-Aldrich), goat anti-GATA3 (1:200, AF2605, R&D systems), rabbit anti-JAG1 (1:200, #ab7771, Abcam), rabbit anti-CDH6 (1:100, #HPA007047, Sigma Aldrich) and goat anti-SYNPO (1:200, #sc-21537, Santa Cruz Biotechnology). Secondary antibodies were: Alexa-488-conjugated goat anti-rabbit, Alexa-594-conjugated donkey anti-rabbit, Alexa-488-conjugated donkey anti-goat and Alexa-594-conjugated goat anti-mouse (1:250, Life Technologies). Images were taken using Nikon Ti-U microscope or Zeiss LSM 510 Meta UV confocal microscope. All IF analyses were successfully repeated more than three times and representative images were shown.

Immunofluorescence

Pellets were fixed with 4% PFA for 10 min at 4° C., embedded in paraffin and sectioned with 7 μm thickness. Sections were blocked with sheep serum for 1 hr at RT then antigen retrieval was performed using Antigen Unmasking Solution (Vector labs). Primary antibodies were incubated overnight at 4° C. and secondary antibodies were incubated for 1 hr at RT. The following antibodies and dilutions were used: rabbit anti-CALB1 (1:200, #C2724, Sigma-Aldrich), rabbit anti-AQP1 (1:200, sc-20810, Santa Cruz Biotechnology), rabbit anti-AQP2 (1:200, AB3274, Millipore), rabbit anti-SLC3A1 (1:100, 16343-1-AP, Proteintech) and rabbit anti-human specific mitochondria (HuMt) (1:800, #ab92824, Abcam). Frozen sections embedded in OCT compound (Sakura) were used for staining with anti-human specific nuclei (HuNu) (1:800, #MAB1281, Merck). Images were taken using Olympus BX-51 microscope or Zeiss LSM 510 Meta UV confocal microscope. All IF analyses were successfully repeated more than three times and representative images were shown.

Gene Expression Analysis

Total RNA was extracted from cells using RNeasy micro kit (QIAGEN) and cDNA was synthesized from >100 ng RNA using Super Script III reverse transcriptase (Life Technologies). Quantitive RT-PCR (qRT-PCR) analyses were performed with Syber Green (Applied Biosystems) by ABI PRISM 7500 real-time PCR machine. All absolute data were firstly normalized to GAPDH then normalized to control samples (delta-delta-Ct method). Conventional RT-PCR analyses were performed using OneTaq DNA polymerase (NEB) as per manufacturer's instruction. All RT-PCR analyses were successfully repeated more than three times and representative images were shown. The sequences of primers used for RT-PCR and qRT-PCR are as listed (Table 1 and Table 2).

Quantitation of Proportion of Induced Cells

To quantify the proportion of differentiated cells positive for PAX2+, LHX1+, SOX17+, SIX2+ or WT1+, cells were immunofluorescently stained with each antibody together with the nuclear stain, DAPI. The ratio of differentiated cells to total cells was manually counted using Image J in 1 or 2 representative fields per experiment (total 3-5 representative fields from 3 independent experiments, $1-1.5 \times 10^3$ cells in total), using an Olympus BX-51 microscope, 10× objective.

3D Cultures hESC-derived induced kidney cells were harvested and dissociated into single cells using TripLE select (Life Technologies) at day 12 to 13 of the differentiation. $10 \times 10^5$ cells were span down at ×400 g for 2 min to form a pellet then placed onto a filter membrane with 0.4 μm pore of 13 mm diameter (#7060-1304 Whatman) with Collagen IV (Becton Dickinson) coat at 10 μg/cm². The filter was floated on the culture media of 10% FCS/DMEM for 4 days.

Re-Aggregation Assay

The re-aggregation assay was performed as previously described.[5,29] Briefly, a filter membrane was coated with Collagen IV (Becton Dickinson) at 10 μg/cm². For preparing the embryonic kidney cells to be recombined, embryonic kidneys from 12.5-13.5 dpc mice were digested with Accutase (Life Technologies) at 37° C. for 10 min and dissociated by manually pipetting. After the cells had been filtered through a 100 μm nylon mesh, $4\text{-}10 \times 10^5$ of embryonic kidney cells were recombined with 4% of hESC-derived cells then centrifuged at ×400 g for 2 min to form a pellet. The pellet was placed on a filter membrane prepared as above and cultured for 4 days with 10% FCS/DMEM culture media.

Results

Figure 2:
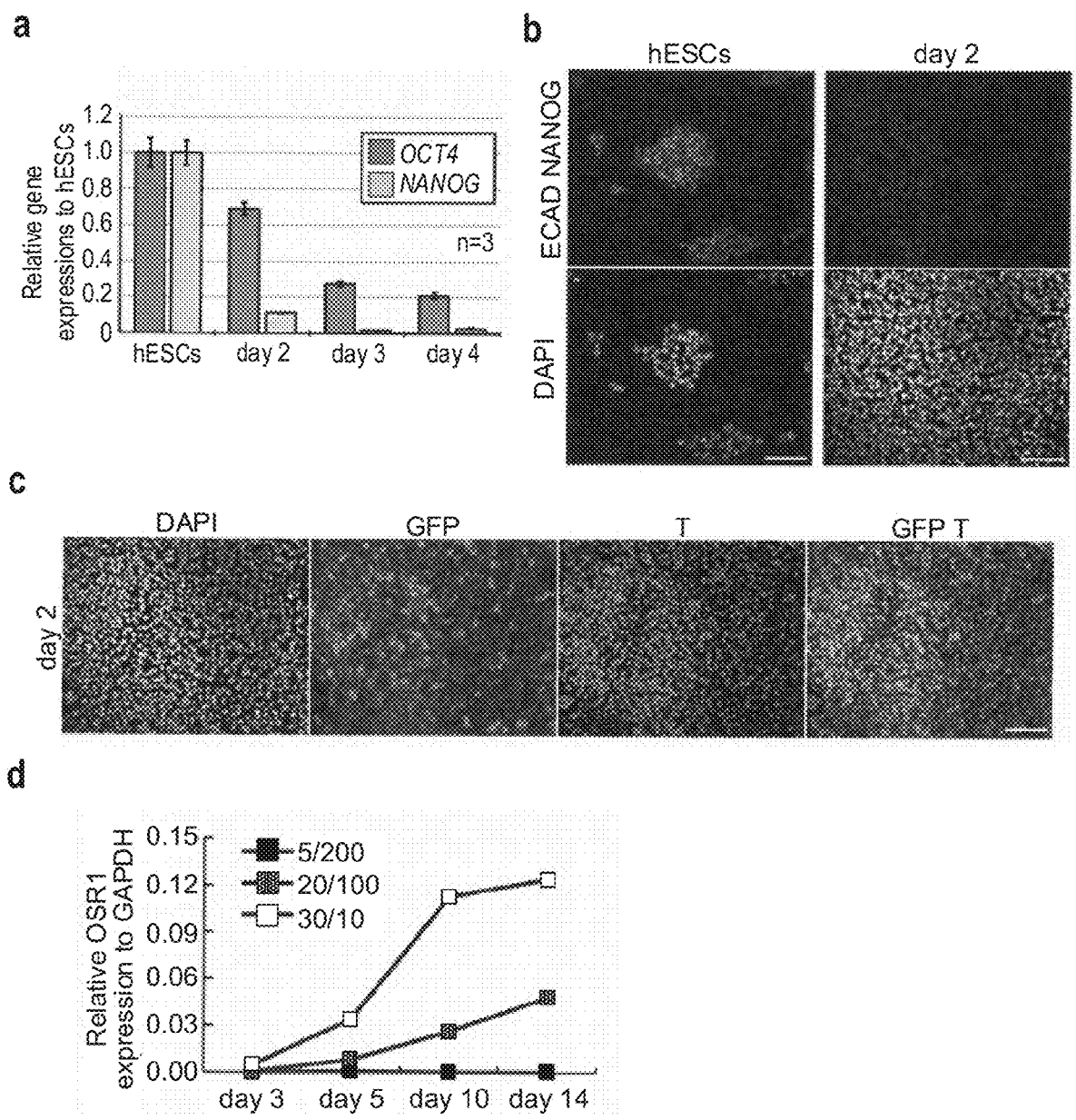
FIG. 2. Posterior primitive streak induction. a, Time course quantitative RT-PCR for pluripotent markers, OCT4 and NANOG after induction with BMP4/ActivinA (30/10 ng/ml), showing a reduction in pluripotent gene expression with time. Error bars are s.d. (n=3 experiments). b, IF for markers of ES cells, NANOG and ECAD, before (hESCs) and after (day 2) posterior primitive streak induction using CHIR99021. (scale=100 µm) c, IF for markers of posterior primitive streak, T and MIXL1 (GFP), after the posterior primitive streak induction (day 2) using CHIR99021. MIXL1 was detected as GFP expression driven by the MIXL1 endogenous promoter. (scale=100 µm) d, Levels of spontaneous OSR1 expression induced across time after culture if 3 different ratios of BMP4 and Activin A (ng/mL). hESCs were formed embryoid bodies with 3 different ratios of BMP4 and Activin A for 3 days then spontaneously differentiated under no growth factor condition until day 14. This demonstrates improved OSR1 expression in cells induced with high BMP4 and low Activin A (30/10). OSR1 marks IM and LPM.

We have defined a three stage framework for the differentiation of hESCs to the key cellular compartments of the developing kidney, including genes that mark or exclude a specific end result[6] (FIG. 1a). The primitive streak, the progenitor population for both mesoderm and endoderm, can be induced from mouse ES cells (mESCs) using Activin A[7] with opposing gradients of BMP4 and Activin A specifying anterior (endoderm) versus posterior (mesoderm) primitive streak in mice[8,9]. Canonical Wnt signalling has also been reported as an inducer for primitive streak in mouse and human ESCs[7,10]. As the IM initially arises from the posterior primitive streak, we first examined if hESCs responded to these morphogens in a similar way to mouse. We have previously shown that 20/100 (ng/mL) of BMP4/Activin A induced GFP+ primitive streak from the reporter hESC line, MIXL1$^{GFP/wt}$, in which GFP is knocked into MIXL1 gene locus, a robust marker of primitive streak[11]. Using this reporter line in monolayer culture, we tested several combinations of BMP4 and Activin A (5/200, 20/100, 30/10, 30/0 and 0/0 ng/mL) or varying concentrations of a canonical Wnt signalling agonist, CHIR99021 (5, 7, 9 μM) for optimal differentiation. All in vitro experiments were performed under chemically defined serum-free culture conditions[12]. Comparative expression of MIXL1, T (posterior primitive streak), and SOX17 (anterior primitive streak), suggested that high BMP4/low Activin A (30/10) or high CHIR99021 (>7 μM) was optimal for posterior primitive streak (FIG. 1 c,d; FIG. 2a-c). Under both conditions approximately 90% of cells became GFP+ (FIG. 1b).

Figure 3:
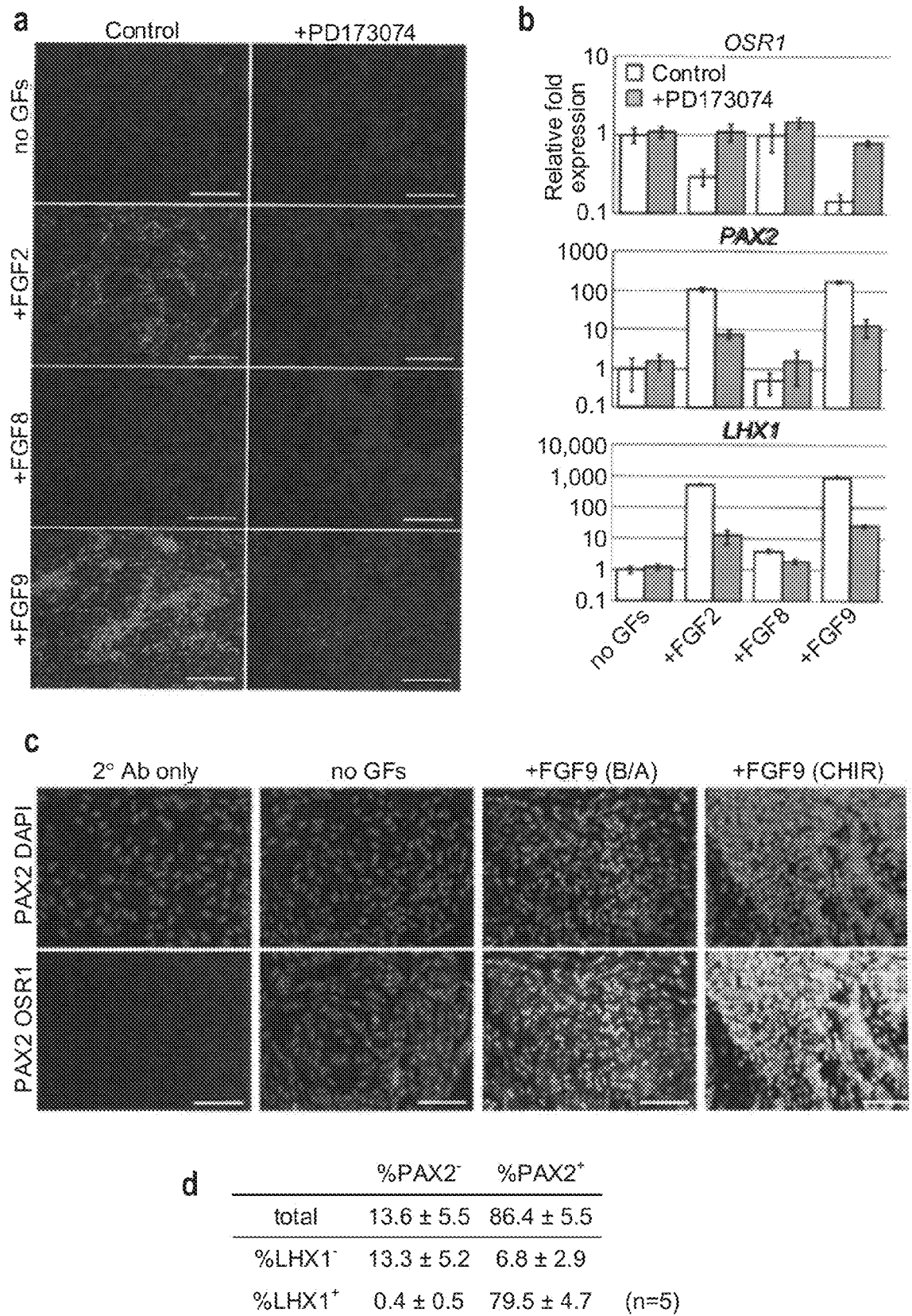
FIG. 3. Influence of FGF signalling on induction of IM proteins. a, IF for PAX2 protein on hESC cultures at day 6 treated with BMP4/Activin A to day 2 and FGF2 (200 ng/ml), FGF8 (200 ng/ml), FGF9 (200 ng/ml) or no growth factors (no GFs) from day 2 to 6 in the presence or absence of the FGF signalling inhibitor, PD173074. (scale=200 µm) b, Quantitative RT-PCR to examine the relative expression level of PAX2, LHX1 and OSR1 at day 6 of the same protocol as IF (a). Shaded bars show the effect of addition of the FGF inhibitor, PD173074. Error bars are s.d. (n=3 experiments). c, IF for the IM marker PAX2 and the marker of both LPM and IM, OSR1, on hESC cultures at day 6 treated with BMP4/Activin A (+FGF9 (B/A)) or 8 µM CHIR99021 (+FGF9 (CHIR)) to day 2 followed by 200 ng/mL FGF9 or no growth factors (no GFs) from day 2 to 6. Secondary antibody only control was used as a negative control (2° Ab only) (scale=100 µm) d, A table showing the percent of PAX2⁻ and PAX2⁺ cells in total (total) or together with LHX1⁻ and LHX1⁺ cells on hESC cultures at day 6 treated with 8 µM CHIR99021 to 2 days followed by 200 ng/mL FGF9 from day 2 to 6. Errors are s.d. (n=5 fields in total from 3 experiments).
Figure 4:
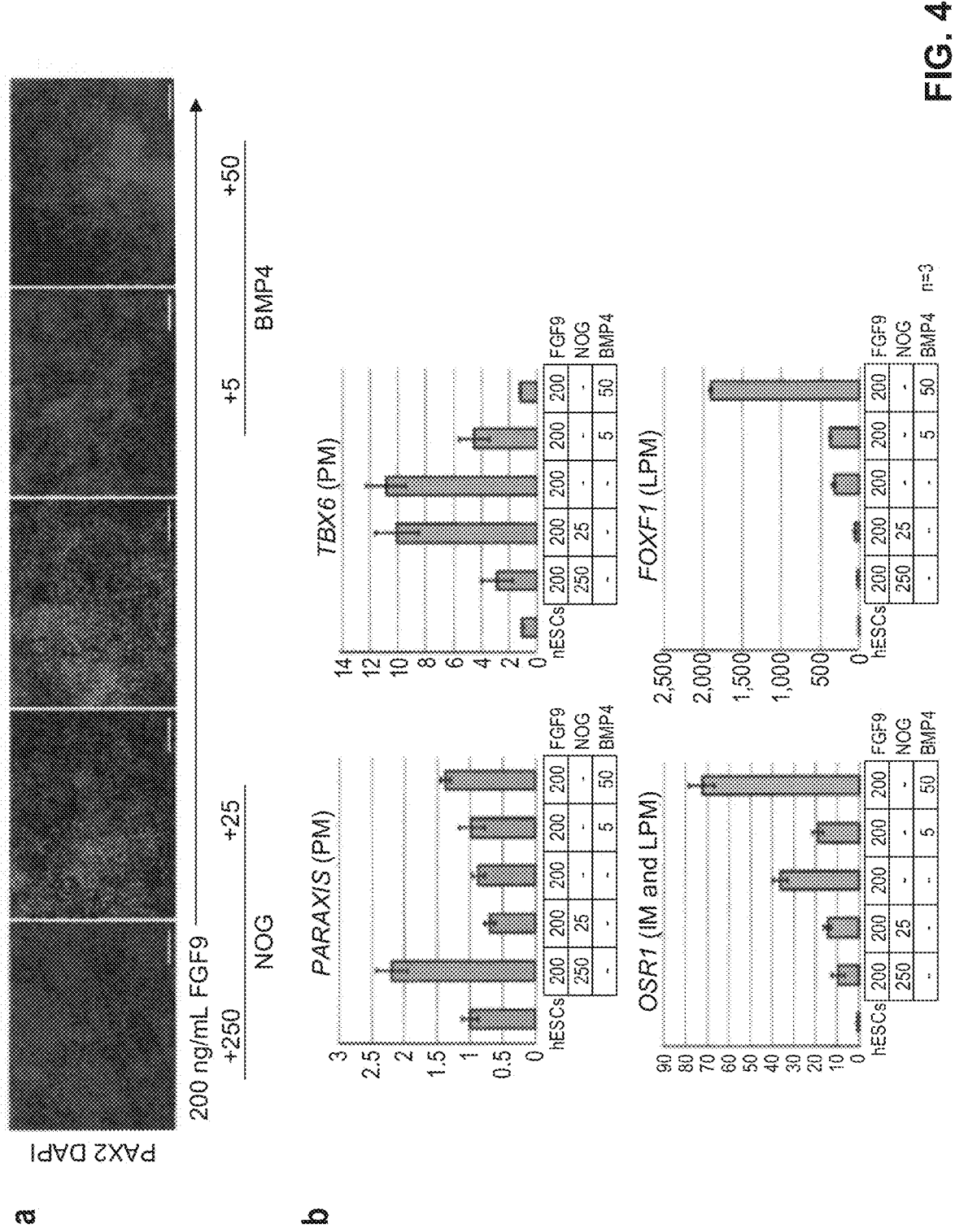
FIG. 4. The effect of BMP signalling on lateral-medial patterning of early mesoderm. a, IF for DAPI (blue) and PAX2 (red) at day 6 in the presence of 200 ng/mL FGF9 with or without BMP4 (5 or 50 ng/mL) or the BMP antagonist NOG (25 or 250 ng/mL) from day 2 to day 6. (scale=200 µm) b, qRT-PCR to investigate the effect of this BMP/NOG gradient on the expression of PM (PARAXIS and TBX6) and LPM (FOXF1 and OSR1) markers at day 6. Error bars are s.d. (n=3 experiments).

The second stage of differentiation was to induce IM from primitive streak. After gastrulation, the definitive mesoderm can give rise to IM, paraxial (PM) and lateral plate mesoderm (LPM). Previous studies investigating renal differentiation of pluripotent cells have relied on OSR1 as a definitive marker of IM and even MM formation[13]. However, OSR1 expression is seen in trunk mesoderm and extends into LPM[14]. Spontaneous differentiation after initial induction of primitive streak (BMP4/Activin A (30/10), 3 days) showed OSR1 expression (FIG. 2d) but no evidence of more definitive IM markers, PAX2 and LHX1[14-16], by either RT-PCR or immunofluorescence (IF). This indicated a need for further growth factors to appropriately direct the next stage. FGF signalling was one possible requirement. FGF8 is expressed from primitive streak through to posterior trunk mesoderm and FGF9 is expressed in IM and PM[17,18]. MM survival in vitro is supported by culture in either FGF2/BMP7[19] or FGF9[20]. We therefore tested the capacity of three FGF family members, FGF2, FGF8 and FGF9, to induce IM from posterior primitive streak. hESC-induced posterior primitive streak was treated with 200 ng/mL of FGF2, 8 or 9 for 4 days before analysis via IF and qRT-PCR (FIG. 1e). In the presence of FGF2 or FGF9, but not FGF8, OSR1, PAX2 and LHX1 were coexpressed with >80% of cells PAX2+, suggesting differential IM induction (FIG. 1f-h). PAX2 and LHX1 induction in response to FGF2 or FGF9 was dramatically inhibited by PD173074, a chemical inhibitor for FGFR1 and FGFR3 (FIG. 3a,b). IM induction by FGF9 was dose-dependent (optimal at 200 ng/ml) with suppression of the LPM markers, FOXF1 (FIG. 1i) and OSR1 (FIG. 3b). Cellular c-localisation of PAX2 and OSR1 proteins was observed after initial induction with either BMP4/Activin A or CHIR99021 followed by FGF9, with LHX1 and PAX2 proteins co-localised in 79.5% (±4.7% s.d.; n=5) of cells (FIG. 3c,d). Hence, an FGF signal is sufficient to efficiently specify IM after posterior primitive streak. In early mesoderm development, BMP signaling is the key morphogen regulating lateral-medial patterning. Low BMP4 induces IM whereas high BMP4 induces LPM and NOG (noggin)-mediated antagonism of BMP signaling is required for PM[21]. We reproduced this patterning in vitro using BMP4 and NOG together with FGF9 (FIG. 1j). Here, FOXF1 was effectively suppressed by NOG while the induction of IM markers PAX2 and LHX1 was sustained only in the presence of FGF9 alone or low NOG (FIG. 1j; FIG. 4a,b). While the PM marker TBX6 behaved in similar way to IM markers (FIG. 4b), expression was low. IF revealed that TBX6+ cells were a minor population completely exclusive of the PAX2+ IM cells (FIG. 1k). The primitive streak can also differentiate into endoderm, however IF showed only 0.244% (±0.099% s.d.; n=5) of cells were positive for the definitive endoderm marker, SOX17, confirming the specificity of differentiation into mesoderm.

Figure 5:
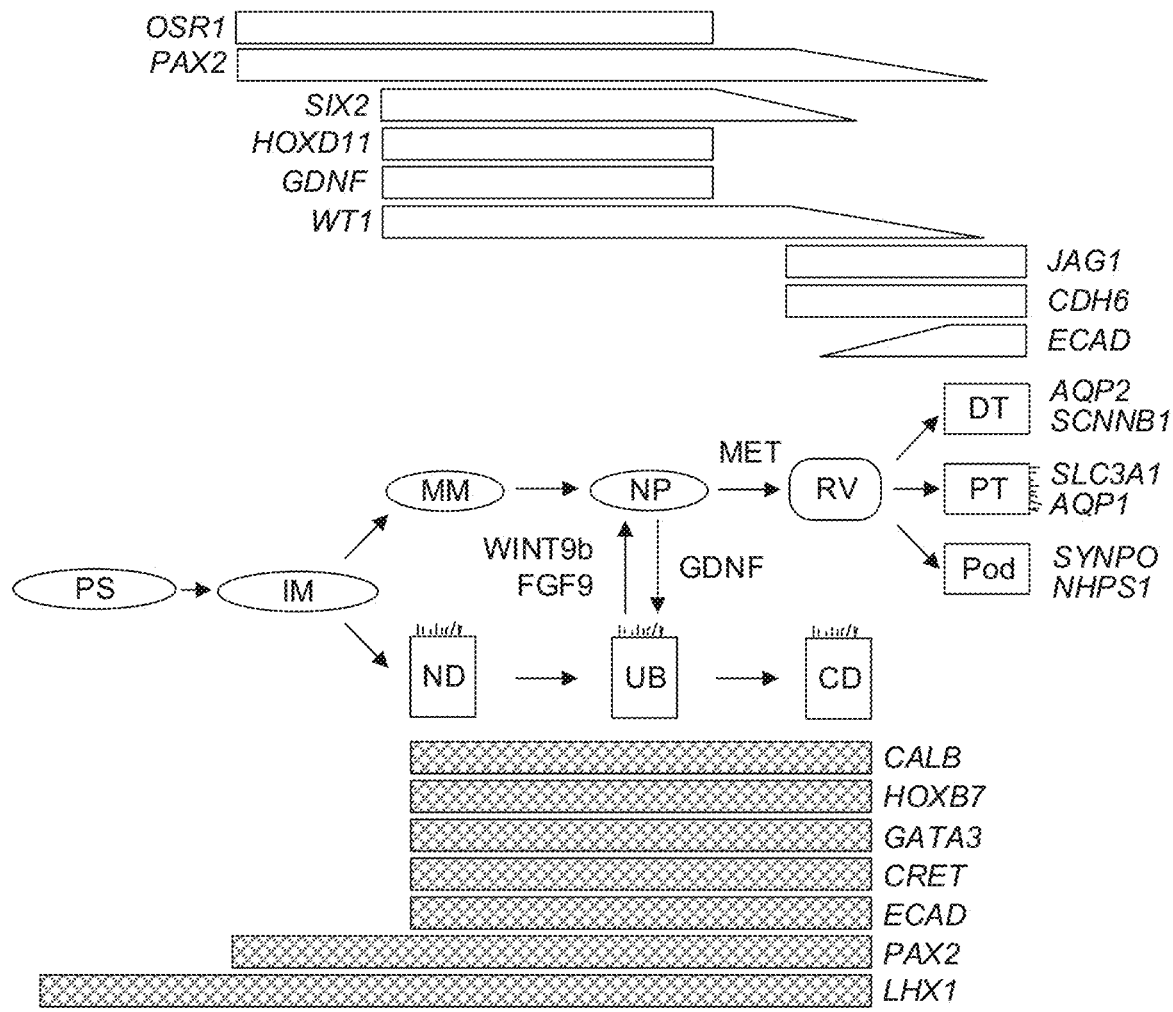
FIG. 5. Schematic illustrating the anticipated gene expression of distinct progenitor and derivative cell populations during early kidney development. PS, primitive streak; IM, intermediate mesoderm; MM, metanephric mesenchyme; NP, nephron progenitor/nephrogenic mesenchyme; RV, renal vesicle; DT, distal convoluted tubule; PT, proximal convoluted tubule; Pod, podocyte; ND, nephric duct; UB, ureteric bud/ureteric epithelium; CD, collecting duct; MET, mesenchymal to epithelial transition. All genes are indicated in italics. Shaded boxes indicate the timing and duration of expression for adjacent labelled genes. Specific genes marking DT, PT and Pod are indicated next to each cell type. The reciprocal induction of differentiation known to occur between the UB and NP is supported by the expression of FGF9 (nephrogenic mesenchyme survival) and Wnt9b (MET) and from the UB and GDNF (ureteric branching) by the NP.
Figure 6:
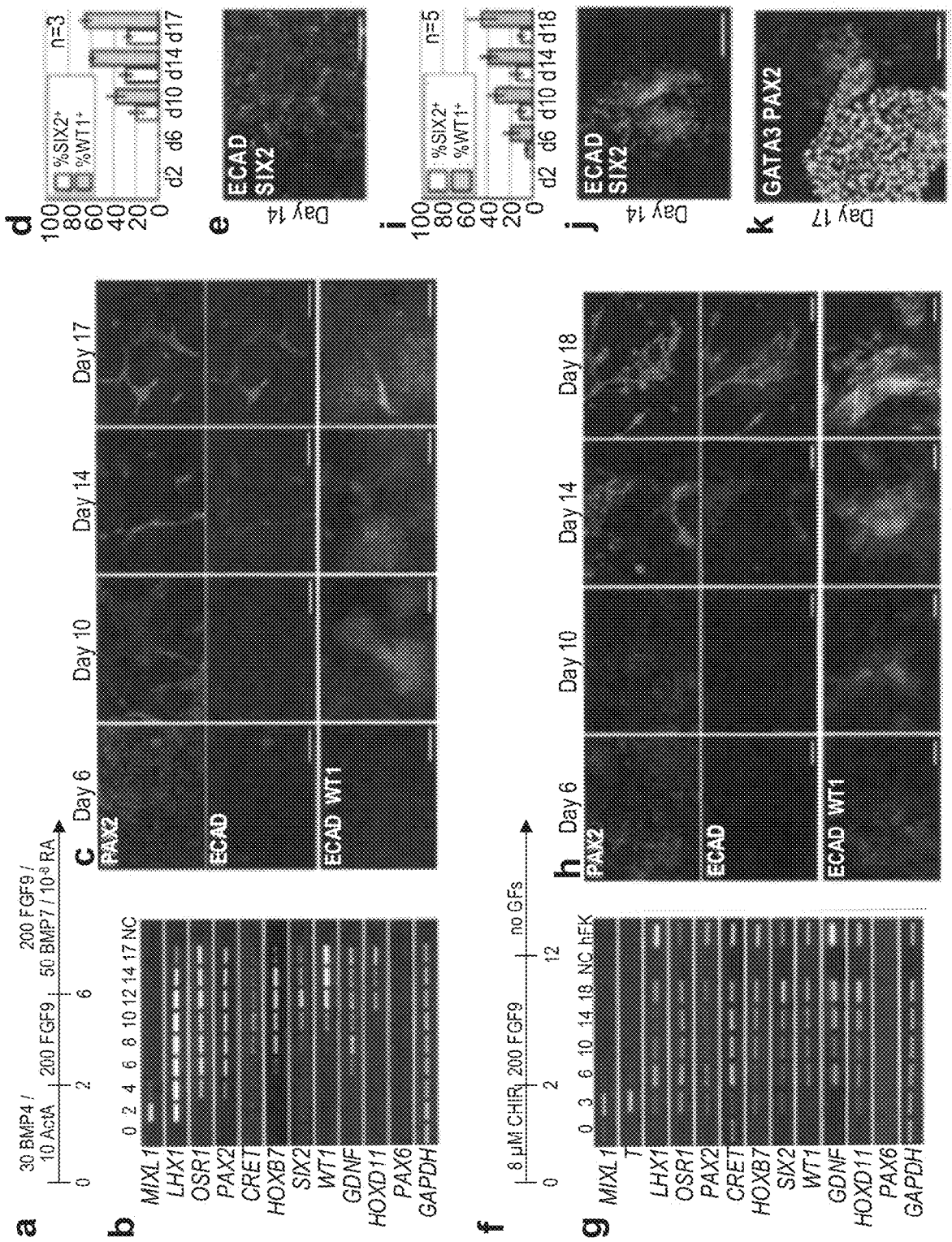
FIG. 6. Stepwise temporal induction of ureteric and metanephric progenitors from hES cells in vitro. a, Schematic representation of the initial hESC directed differentiation protocol used to induce kidney development (BMP4: Activin A/FGF9/FGF9:BMP7:RA). Numbers below the line indicate the days of the differentiation. b, Timecourse RT-PCR from day 0 to 17 for genes representing each stage of differentiation to kidney. These include genes for posterior primitive streak (MIXL1, LHX1), IM (LHX1, PAX2, OSR1), MM (OSR1, SIX2, WT1. GDNF, HOXD11) and UE (PAX2, CRET, HOXB7). PAX6 was included to ensure that there was no evidence for ectodermal commitment. NC, negative control with no DNA template. c, Timecourse IF from day 6 to 17 showing the formation of PAX2 (red) and ECAD (green) double positive epithelial structures (upper panels) and WT1 (red) positive populations surrounding these epithelial structures (lower panels). (scale=200 µm) d, Quantitation of the proportion of WT1⁺ or SIX2⁺ cells present within hESC cultures across the directed differentiation timecourse. Co-expression of these proteins marks the MM/nephron progenitor (NP) population whereas WT1 protein is also expressed in subsequently differentiating nephrons. Error bars are s.d. (n=3 experiments). e, Day 14 of the differentiation revealed the presence MM (ECAD⁻ SIX2⁺) around an ECAD⁺ UE. (scale=200 µm) f, Schematic representation of the alternative hESC directed differentiation protocol used to induce kidney development (CHIR99021/FGF9). Numbers below the line indicate the days of the differentiation. g, Time course RT-PCR from day 0 to 18 via differentiation using CHIR99021/FGF9 representing each stage of differentiation to kidney as indicated in (b). h, Timecourse IF from day 0 to 18 via differentiation using CHIR99021/FGF9 for proteins as indicated in (c). (scale=200 μm) i, Quantitation as described in (d) after differentiation using CHIR99021/FGF9. Error bars are s.d. (n=5 fields in total from 3 experiments). j, The presence of SIX2$^+$ condensed mesenchymal cells surrounding ECAD$^+$ UE structures at day 14. (scale=100 μm) k, IF microscopy at day 17 showing PAX2$^+$GATA3$^+$ UE at day 17 adjacent to a region of PAX2$^+$GATA3$^-$ MM. (scale=50 μm)
Figure 7:
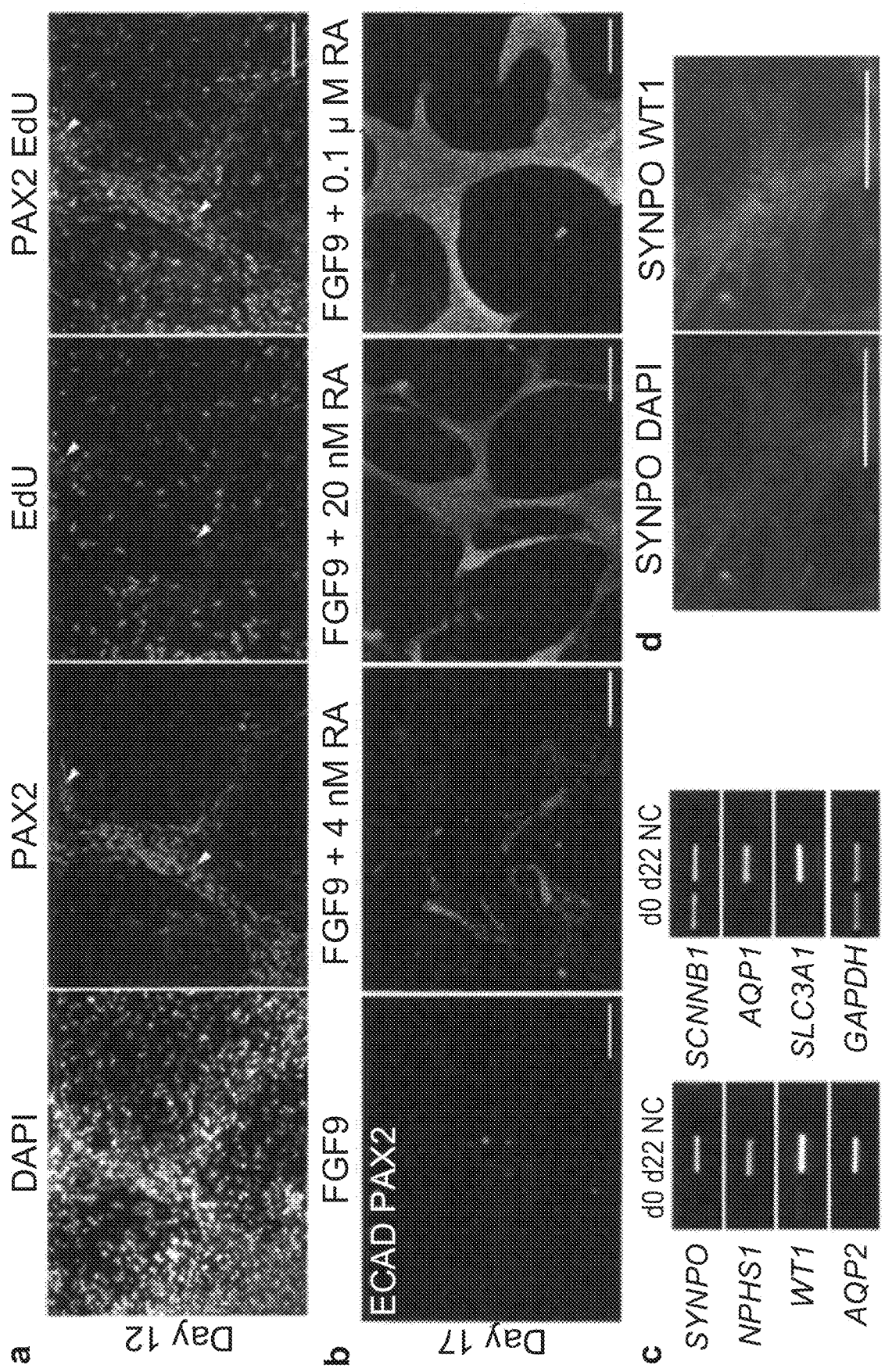
FIG. 7. The positive effect of RA on ureteric epithelium formation. a, EdU incorporation assay at day 12 of differentiation. 30 min exposure by EdU revealed that not only PAX2$^+$ pre-epithelium structures but also PAX2 negative cells are proliferating. White arrowheads indicate EdU incorporation in PAX2$^+$ cell. (scale=100 μm) b, IM cells at day 6 after posterior primitive streak induction using BMP4/Activin A were cultured for 11 days with FGF9 together with different RA concentrations. IF for UE markers, PAX2$^+$ ECAD$^+$, showed UE structures were induced in a RA dose-dependent manner. (scale=200 μm) c, RT-PCR at day 22 of differentiation using BMP4:Activin A/FGF9/FGF9: BMP7: RA protocol revealed the expression of genes indicative of differentiation into mature renal cell types, including SYNPO, NPHS1 and WT1 for podocyte; AQP2 and SCNNB1 for distal tubule or collecting duct and AQP1 and SLC3A1 for proximal tubule. NC, negative control with no DNA template. d, IF of day 22 differentiation using BMP4/Activin A showing co-expression of two key podocyte markers; the slit-diaphragm protein SYNPO (green) and nuclear WT1 (red). Nuclei are also stained with DAPI (blue). (scale=50 μm)

In mammals, the IM differentiates into the kidney, gonad and the adrenal. The first structure to form is the nephric duct (ND) along which three paired excretory organs form (pronephros, mesonephros and metanephros in order from head to tail) from the same nephrogenic cord. Only the metanephros, representing the final permanent kidney, persists post birth. Key in the formation of the metanephros is reciprocal inductive events between key cellular components (FIG. 5). The MM drives the outgrowth of the ureteric bud (UB)/ureteric epithelium (UE) via the production of GDNF. The UE promotes the survival of the MM via the production of FGF9 and induces nephron formation via Wnt signaling. After formation, each nephron elongates and segments to form the many functionally distinct cell types that comprise the nephron (FIG. 5). Based on the evidence that retinoic acid (RA) can promote ureteric epithelium outgrowth[22], RA and BMP7 have previously been shown to induce renal lineages from mESCs[23] and FGF9 can maintain mouse nephron progenitors in vitro[20], we added 200 ng/mL FGF9, 50 ng/mL BMP7 and 0.1 nM RA from day 6 to day 17 after an initial induction using BMP4/Activin A (FIG. 6a). RT-PCR across the entire differentiation protocol (FIG. 6b) revealed the stepwise differentiation from primitive streak (MIXL1, LHX1) to IM (OSR1, PAX2, LHX1) then MM (SIX2, WT1, GDNF, HOXD11). The expression of HOXD11 indicated metanephros rather than mesonephros[24]. Importantly, the simultaneous induction ND/UE genes (C-RET[25] and HOXB7[26]) was also observed (FIG. 6b). Indeed, IF demonstrated the formation of ECAD+PAX2+ epithelial structures from day 14 (FIG. 6c). The formation of these early epithelial structures was promoted by RA in a dose dependent manner (FIG. 7b), also supporting an identity of UE[22,27]. Both this population and the surrounding mesenchyme showed evidence of proliferation in vitro (FIG. 7a). As in the developing kidney, an initial mesenchymal field positive for SIX2 and WT1 surrounded the ECAD+ UE structures (FIG. 6c,e) with this population peaking in prevalence at day 14 (FIG. 6d). The percentage of WT1+ cells continued to increase after this time, possibly reflecting the expression of this protein in both nephron progenitors and more differentiated nephron structures (FIG. 6c). RT-PCR at day 22 revealed evidence for further differentiation based on the expression of podocyte (SYNPO, NPHS1 and WT1), proximal tubule (AQP1 and SLC3A1) and collecting duct genes (AQP2 and SCNNB1) (FIG. 7c). IF confirmed the simultaneous presence of WT1 and SYNPO proteins, suggesting the formation of podocytes (FIG. 7d) although early nephron markers were not evident.

Figure 8:
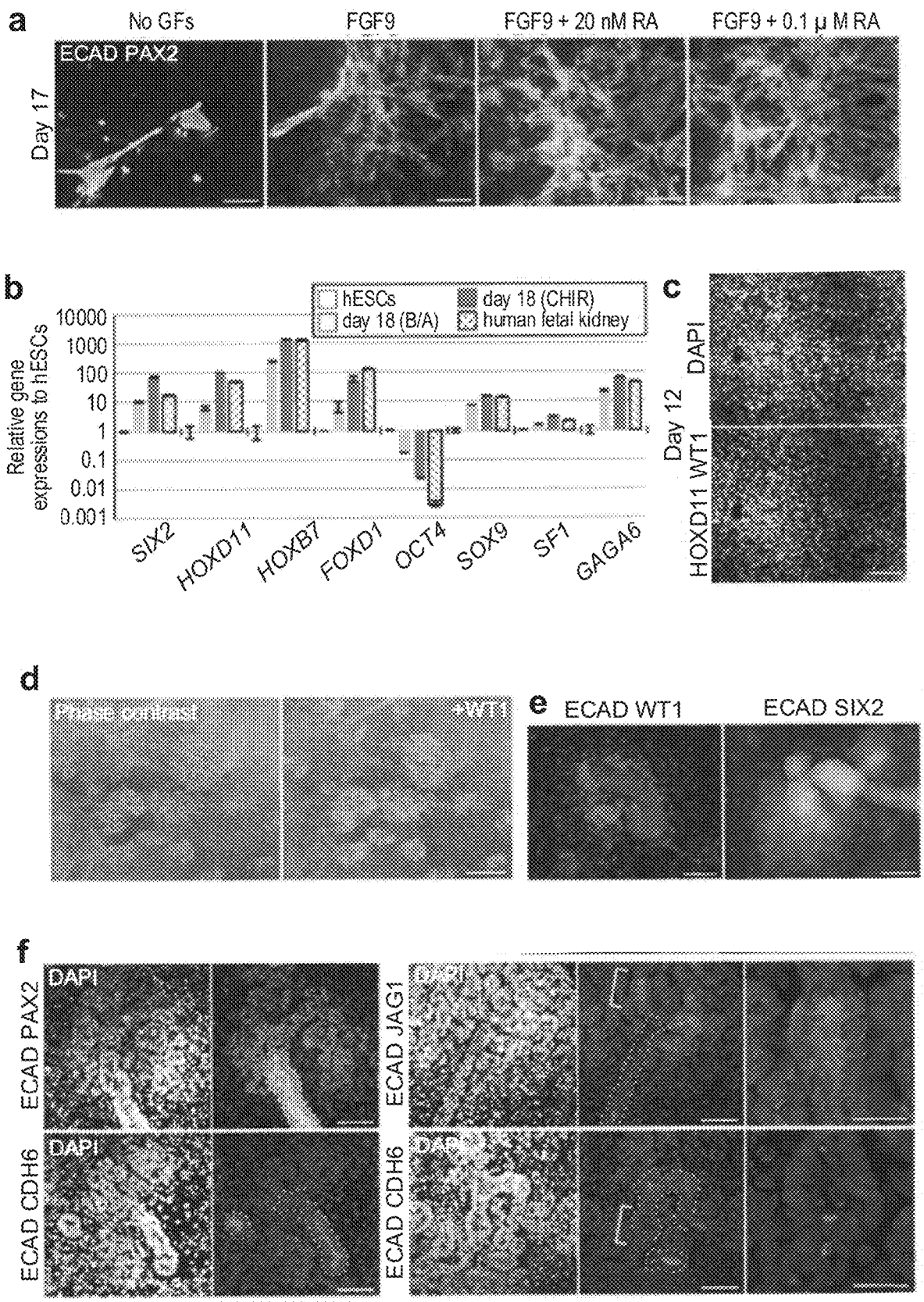
FIG. 8. Assessment of renal potential and evidence for nephron induction of hESC after CHIR99021/FGF9 directed differentiation. a, hESC-derived cells at day 12 of differentiation after initial induction using CHIR99021/FGF9 to day 6 followed by a further 5 days with FGF9 together with different RA concentrations or without growth factors (No GFs). IF for PAX2 and ECAD proteins showed UE structures were induced in RA dose-dependent manner. (scale=200 μm) b, qRT-PCR for major kidney markers (SIX2, HOXD11, HOXB7, FOXD1), a pluripotent marker (OCT4) and gonad/adrenal cortex markers (SOX9, SF1, GATA6). Gene expression levels at day 18 of differentiation using either the BMP4/Activin A (B/A) or CHIR99021 (CHIR) protocol were normalized to GAPDH and then compared to levels in undifferentiated hESCs. Human fetal kidney RNA was used as a positive control. Error bars are s.d. (n=3 experiments). c, IF showing that at day 12 of induction, some WT1$^+$ MM cells (red) were also HOXD11$^+$ (green). HOXD11 is a specific marker of metanephric region, including both the MM and the renal stroma (HOXD11$^+$WT1$^-$). (scale=200 μm). d, Low magnification view of cultures after day 18 of differentiation (CHIR99021/FGF9) using phase contrast and IF for WT1 (red). Clusters of WT1$^+$ mesenchyme surround the UE as would be seen in an embryonic kidney (scale=200 μm) e, WT1$^+$ and SIX2$^+$ mesenchyme (red) tightly surrounding ECAD+UE (green) at day 18. (scale=50 μm) f, IF confocal microscopy at day 18 showing PAX2$^+$ECAD$^+$ UE surrounded by early nephrons/RVs as assessed by the presence of JAG1 and CDH6. The areas surrounded by dashed line are PAX2$^+$GATA3$^+$ECAD$^+$ UE structures. The areas indicated by square bracket are magnified in next right panels. (scale=25 μm) (magnified scale=10 μm).

These data suggest the coordinated differentiation of the multiple interacting cellular compartments required for kidney development. While previous studies have used RA and BMP7 in induction protocols, our data would suggest that this may not be optimal for further differentiation. We base this on the transient expression of SIX2, presence of a dispersed mesenchyme and no evidence for mesenchymal PAX2 expression, a feature of MM in the developing kidney. Addition of RA/FGF9 after an initial CHIR99021 induction generated strong UE at the expense of condensed PAX2+ MM around UE (FIG. 8a). In contrast, prolonged differentiation in FGF9 alone (note the removal of all factors after day 12; FIG. 6f) also induced the stepwise induction of PS, IM and both MM/UE but with a faster induction of kidney markers and a more prolonged expression of MM genes, such as SIX2 (FIG. 6g,h,i). Another UE marker, GATA3, was co-expressed in the PAX2+ UE and, more importantly, the MM appeared to condense tightly around the UE tips as is seen in the developing kidney (FIG. 6h,j,k). Critically, this protocol showed evidence for PAX2 expression in both the mesenchyme and the UE (FIG. 6k) more indicative of nephrogenic potential. Finally, the expression of HOXD11 in both WT1+ and WT1" cells demonstrates the additional presence of renal stroma (FIG. 8c), also supported by expression of FOXD1 (FIG. 8b).

Figure 9:
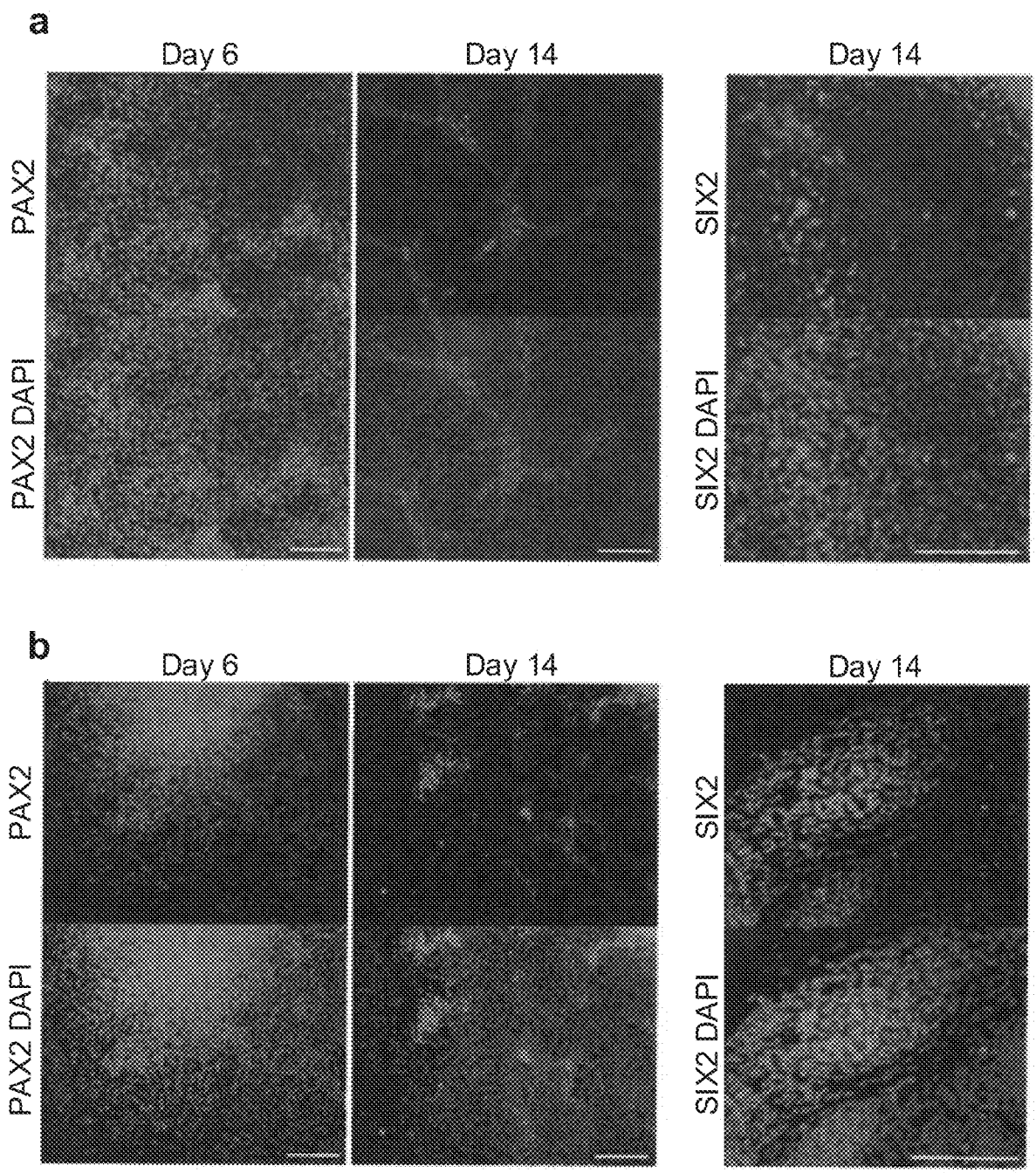
FIG. 9. Differentiation of H9 hES cell line and iPS cell line towards renal lineages.
a, b, Immunofluorescence for DAPI (blue), PAX2 (red) or SIX2 (red) at Day 6 and Day 14 of differentiation on H9 hESC (a) and CRL2429 C11 iPS cells (b). (scale=200 μm)

During embryogenesis, IM also gives rise to gonad and adrenal cortex. The expression levels of markers for these tissues were no higher than is seen in human fetal kidney (FIG. 8b) suggesting that these alternative fates are not significantly selected. The transferability of this differentiation protocol from one hESC cell line to another was investigated using the H9 hESC cell line and human iPS cell line CRL2429 C11 (FIG. 9). The initial induction of posterior primitive streak, subsequent induction of IM in response to FGF9 and onward differentiation was also observed using these cell lines.

The formation of what appeared to be all requisite cell populations for kidney development suggested the potential for these cells to signal between each other to generate a self-organising tissue. Critically, this must include the formation of nephrons. To further assess the ability for this to occur, we initially examined the spontaneous differentiation of these pseudo-2D cultures using our CHIR99021/FGF9 induction protocol followed by withdrawal of growth factors from day 12-18 (FIG. 8d-f). By day 18, elongating ECAD+ UE was surrounded by clumps of mesenchyme positive for three MM markers, WT1, SIX2 and PAX2 (FIG. 8d-f). This MM formed what appeared to be early nephrons/renal vesicles (RVs) as indicated by JAG1 and CDH6 protein (FIG. 8f; FIG. 5). We also observed the formation of lumens connecting UE and RV as occurs in vivo during nephron maturation (FIG. 8f, lower right).

Figure 10:
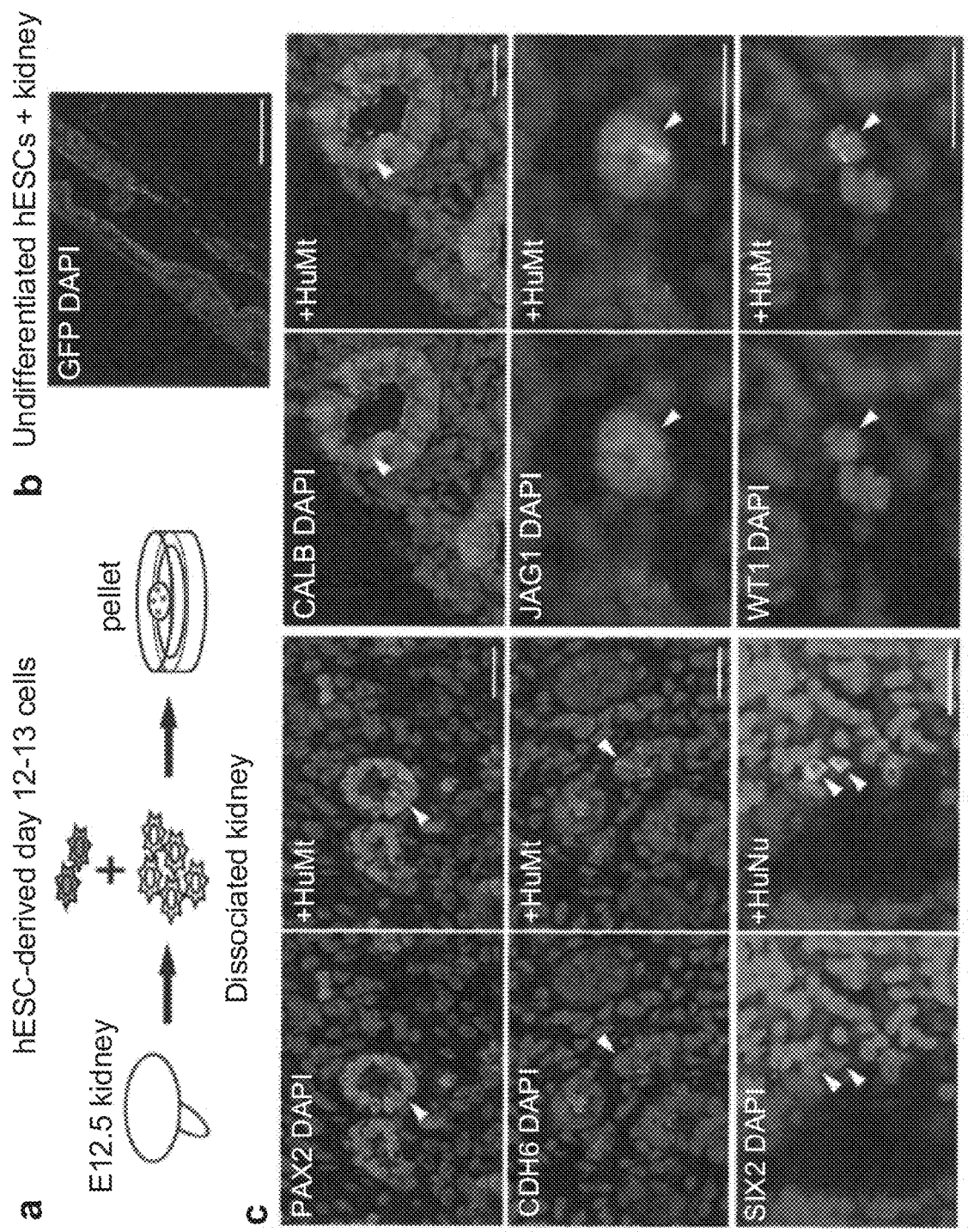
FIG. 10. The integration of hESC-derived kidney progenitors into re-aggregates of mouse kidney cells. a, Schematic of the re-aggregation assay of renal potential. Embryonic day 12.5-13.5 mouse kidneys were dissociated into single cells and combined with hESC-derived induced kidney cells of day 12-13, pelleted onto a filter membrane and cultured at an air-media interface for 4 days. The ratio of hESC-derived cells to mouse kidney cells was 4 to 96. b, Re-aggregation assay using undifferentiated hESC constitutively expressing GFP (ENVY cell line) as a negative control, showing undifferentiated hESC-derived large cysts formation (green). (scale=200 μm) c, Re-aggregation assay of mouse E12.5-13.5 kidney cells with hESC-derived day 13 of the differentiation. All integrated hES cells-derived cells were detected by either human mitochondria antibody (HuMt) or a human nuclear antibody (HuNu) (green). White arrowheads indicate integrated human cells into mouse renal structures. PAX2$^+$ and CALB$^+$ tubules represent UE. CDH6$^+$ and JAG1$^+$ structures represent renal vesicles. SIX2$^+$ and WT1$^+$ non-epithelial cells represent MM/NP. All images show integration of hESC differentiated using the CHIR99021/FGF9 protocol with the exception of the integration into CALB$^+$ UE and SIX2$^+$ MM where the hESC were differentiated using the BMP4:Activin A/FGF9/FGF9: BMP7:RA protocol. (scale=50 μm)

Nephron formation progresses post-RV via a complicated process of segmentation, patterning and differentiation with the expression of specific markers defining the identity and function of each nephron segment from the glomerulus through proximal tubule to distal tubule (FIG. 5). To test for functional integration into kidney tissue, we used a previously characterized re-aggregation assay which represents a stringent assay of the renal potential of a test population[7,28,29] (FIG. 10a). In this assay, mouse embryonic kidneys were dissociated to single cells then re-aggregated with either undifferentiated hESC (control) or hESC at day 12-13 of renal differentiation. After 4 days of culture as re-aggregates, these were sectioned and examined using IF. Cells derived from hESCs were identified using an antibody to human mitochondrial DNA (FIG. 10c arrowheads). hESC-derived cells induced using the CHIR99021/FGF9 protocol integrated into all major cellular compartments of the developing kidney, including PAX2$^+$CALB$^+$ UE (upper panels), CDH6$^+$JAG1$^+$ early nephron/RV (middle panels) and the SIX2$^+$WT1$^+$ nephron progenitor mesenchyme (lower panels), while hESC-derived cells induced using BMP4:Activin A/FGF9/FGF9:BMP7:RA only incorporated into MM and UE. Such integration did not occur in re-aggregations including undifferentiated hES cells. Instead, this resulted in the complete disruption of renal development and the formation of large cysts lined with hES-derived epithelium (FIG. 10b).

Figure 11:
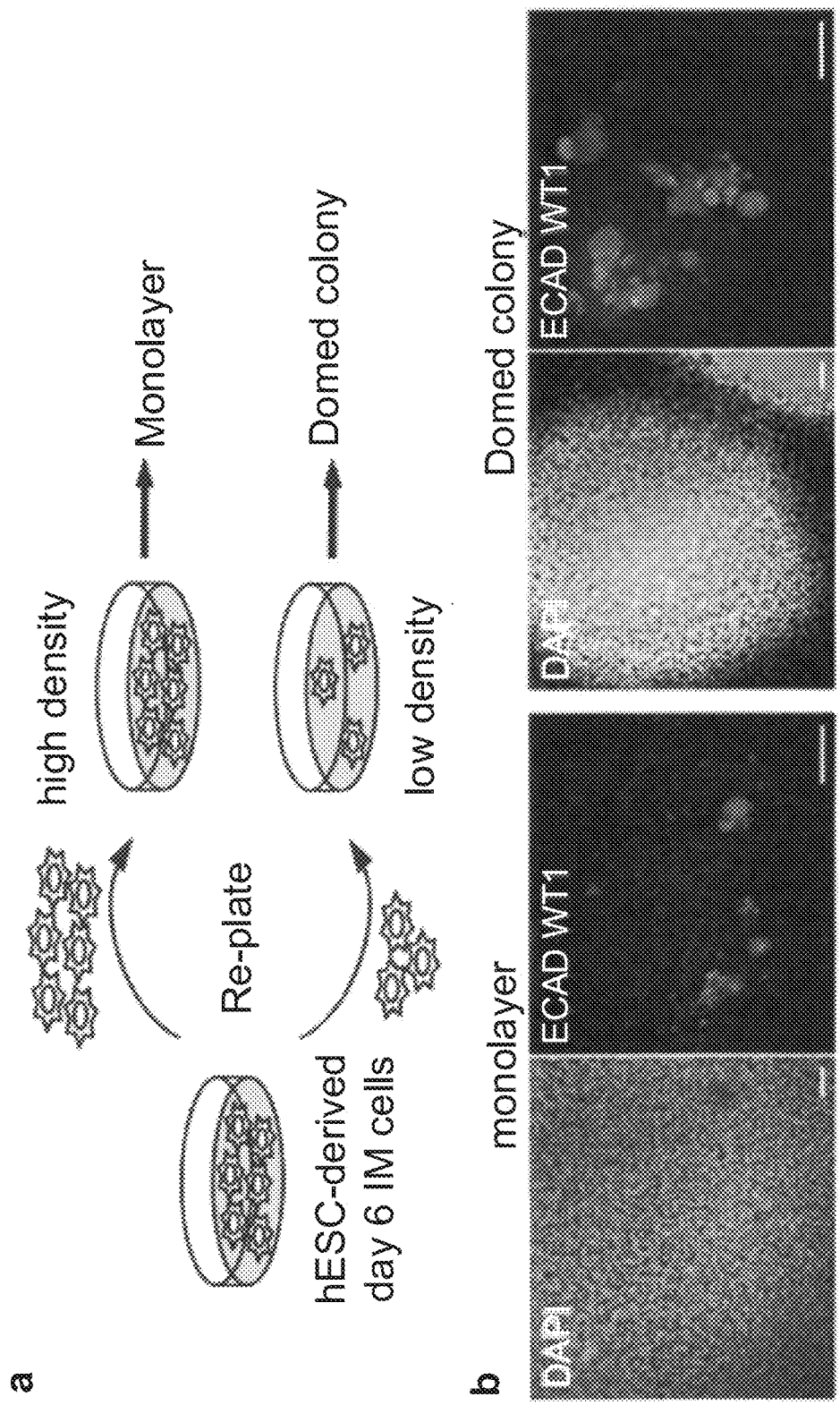
FIG. 11. The effect of 3D culture environment on self-organisation events. a, Schematic of the replating assay. IM cells at day 6 were harvested and re-plated at high density or low density. Then cells were cultured for 12 days (6 days with 200 ng/mL FGF9 then another 6 days without growth factors). Cells plated at high density formed a uniform layer of cells while those plated at low density formed domed colonies. b, Induced IM cells at day 6 were re-plated to form monolayer or domed colonies at day 18. Cells were stained with ECAD for UE and WT1 for MM. More advanced structures are seen within domed colonies possibly due to the proximity of reciprocally inductive cell populations. (scale=100 μm)

In vivo, the kidney forms in three dimensions. Isolated embryonic kidneys can grow as organoids at an air-media interface, successfully forming a branching ureteric epithelium in response to a surrounding MM and undergoing nephron formation, patterning and early segmentation. hESC differentiation was performed as monolayers which may represent an adverse environment for self-organisation and morphogenesis. To test the effect of the shape of cultures on self-organisation, we lifted and replated the differentiating hESC cultures after IM commitment (day 6) at differing cell density (FIG. 11a) followed by continued culture as per the CHIR99021/FGF9 protocol. At day 18, cultures replated at higher density formed a uniform monolayer while those replated at lower density created many small, domed organoids separated across the plate. While WT1$^+$ MM and ECAD$^+$ UE were present under both conditions, the smaller domed colonies formed closely packed and more advanced structures (FIG. 11b) suggesting that the more 3D environment enhanced self-organisation.

Figure 12:
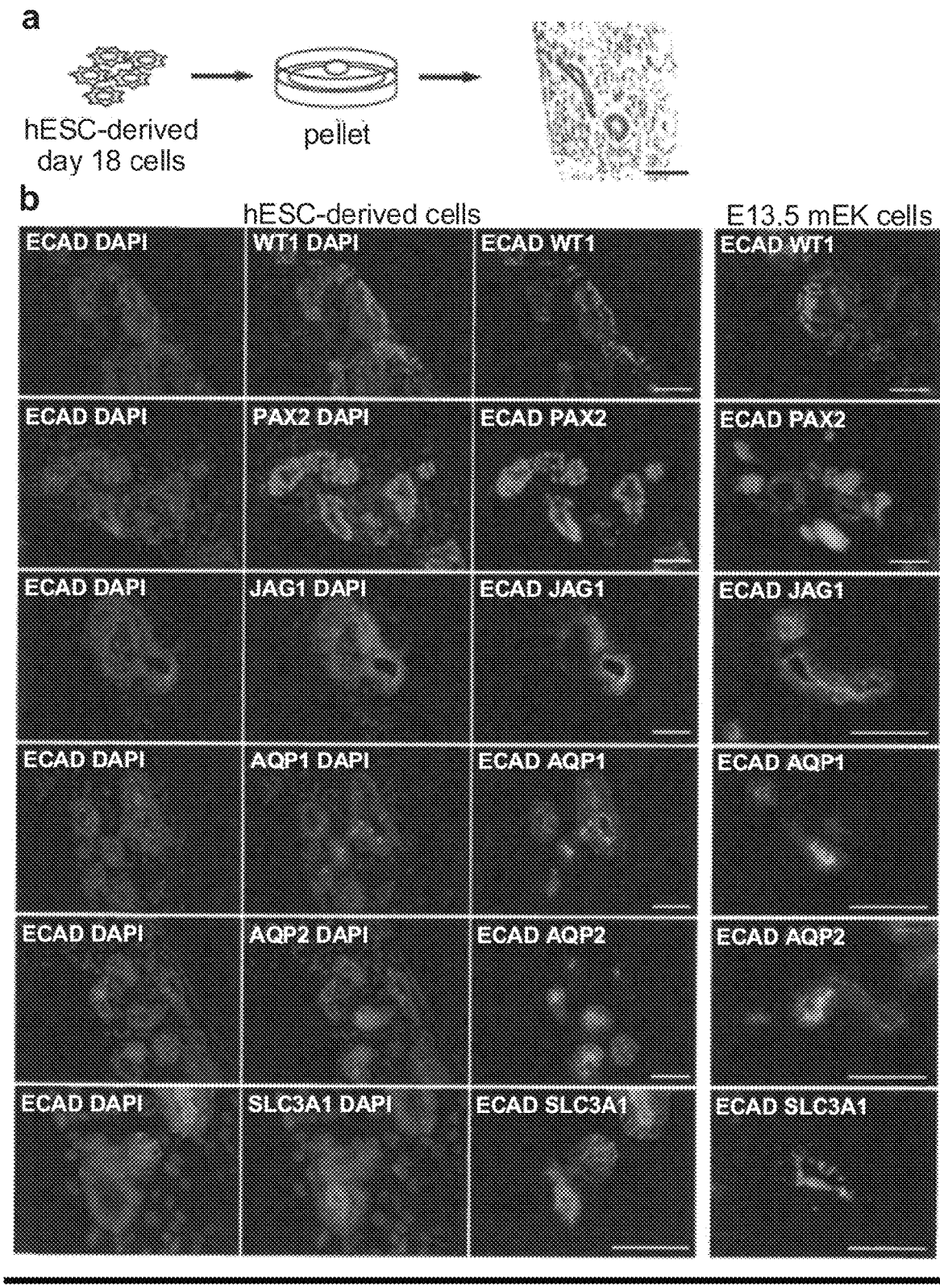
FIG. 12. Evidence for self-organisation after 3D culture of differentiated hESC. a, Schematic of the process used for 3D culture. hESC-derived cells after day 18 of differentiation (CHIR99021/FGF9) were harvested and dissociated into single cells, pelleted then cultured on a filter membrane at an air-media interface with 10% FCS/DMEM. After 4 days culture, pellets were paraffin embedded and sectioned. (scale=200 μm) b, IF of paraffin embedded sections of the 3D cultured pellets showing the expression of a variety of key proteins (hESC-derived cells). ECAD (green) illustrates the presence of epithelium. PAX2$^+$ epithelium represents UE whereas PAX2$^+$ non-epithelium indicates MM and its derivatives. The co-expression of AQP2 with ECAD represents the formation of a derivative of UE, the collecting duct. WT1 staining shown here marks MM/NP. Epithelial derivatives of MM/NP include the renal vesicle, marked by JAG1 and proximal tubule, marked by AQP1 and SLC3A1. As a control, mouse embryonic day 13.5 kidney cells were dissociated and pelleted then cultured in the same way as hESC-derived cells before being analysed (E13.5 mEK cells). (scale=25 μm).

If all requisite cell populations are present for kidney morphogenesis, hESC cultures directed towards kidney differentiation should be able to form kidney organoids in the absence of any other supporting cells. To test this, hESC cultures differentiated to day 18 were enzymatically dissociated then pelleted via centrifugation before 4 days of explant culture (FIG. 12a). This represents standard culture conditions for embryonic mouse kidney explants cultures (10% FCS/DMEM without growth factors). Histological analysis of the resulting pellets revealed ECAD$^+$ tubules that displayed either co-IF for the UE markers PAX2 and AQP2, or the proximal tubule markers AQP1 and SLC3A1. The presence of WT1$^+$PAX2$^+$ MM surrounding the ECAD$^+$ UE was also observed, as was evidence for JAG1$^+$ECAD$^+$ RV formation (FIG. 12b hESC-derived). All of these structures were indistinguishable from the same structures formed via the dissociation and re-aggregation of normal mouse embryonic kidney (FIG. 12b E13.5 mEK), verifying the genuine self-organisation capacity of the cells present after the CHIR99021/FGF9 directed differentiation protocol. Pellets from three independent experiments were analysed with 83% revealing self-organising structures (5/6 pellets). The same level of differentiation was not observed after BMP4:Activin A/FGF9/FGF9:BMP7:RA.

The method disclosed herein method facilitates simultaneous induction of both nephron-forming mesenchyme and ureteric epithelium, which includes and results from interaction between these developing cells and tissues. Both cell and tissue types form to varying degrees even with FGF9 alone through Stages 2 and 3. The addition of other factors such as BMP7, RA and Wnt agonist will vary the outcome in terms of the relative abundance of mesenchyme and the ureteric epithelium produced.

Figure 13:
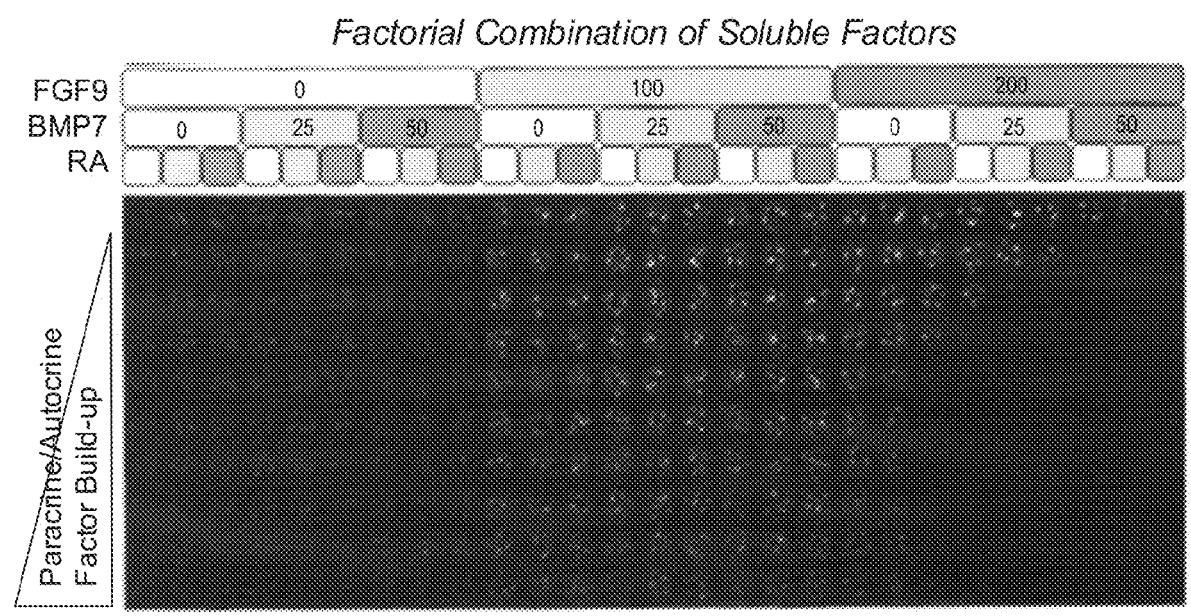
FIG. 13. Evidence that a microbioreactor can be used for the factorial optimization of exact growth factor concentrations required for differentiation to nephron progenitors and/or ureteric epithelium. This microbioreactor comprises 27 rows of 10 wells with each row being subjected to a distinct combination of three different growth factors, FGF9, BMP7 and retinoic acid. The readout is immunofluorescence for E-cadherin (blue, epithelium), GATA3 (green, ureteric epithelium) and WT1 (red, nephron-forming mesenchyme).

To optimally produce mesenchyme and nephrons, FGF9 in Stage 2 is enough to pattern the next step, but the addition of BMP7 together with FGF9 in Stage 3 slightly improves the mesenchyme but more importantly makes the ureteric tree less "sheet-like". It is also proposed that too much FGF9 is ultimately not optimal. This has been assessed in microbioreactor studies, the results of which are shown FIG. 13.

With respect to RA, increasing RA increases the production of ureteric epithelium at the expense of mesenchyme (i.e produces more inappropriate GATA3+ mesenchyme).

Figure 14:
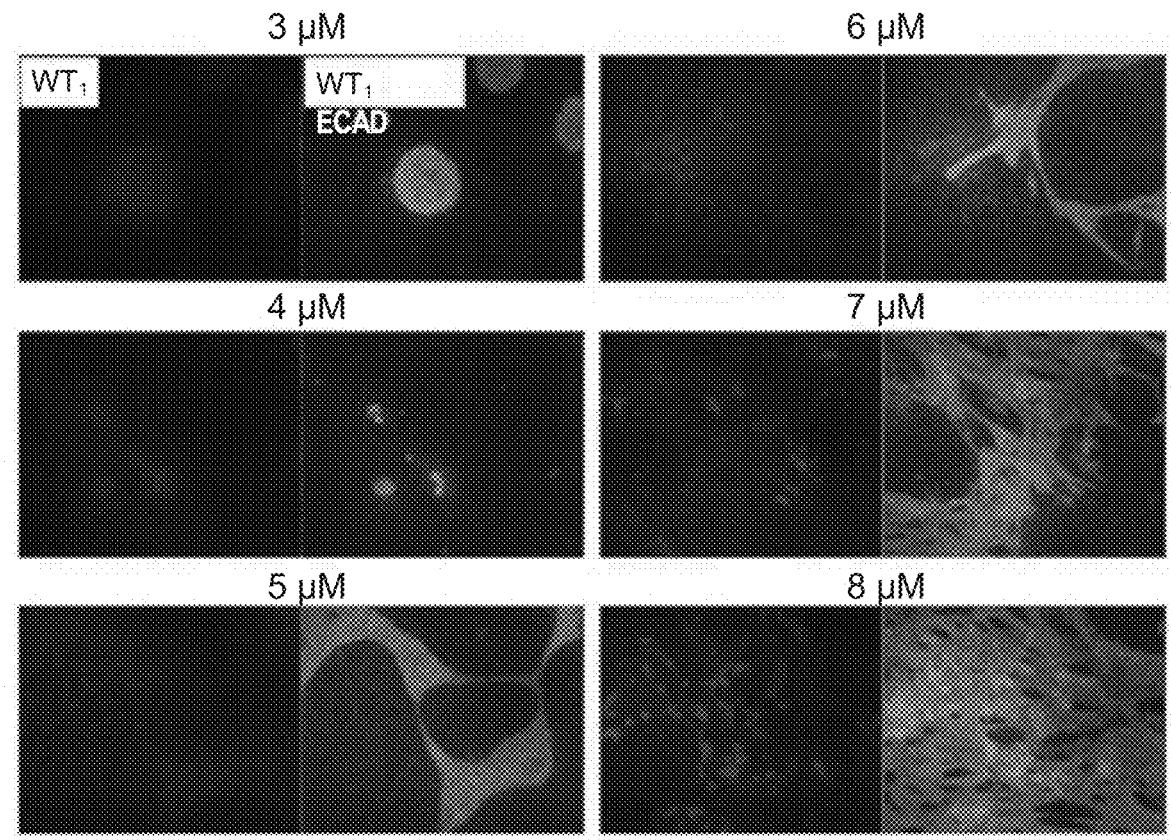
FIG. 14. Optimization of Stage 1 differentiation, as assessed by the ultimate differentiation of these cultures after the completion of subsequent stages of induction. Increasing CHIR99021 in Stage 1 increases the amount of E-cadherin positive (green) ureteric epithelium with an optimal ratio of epithelium to nephron progenitors (marked with antibody to WT1 in red) at 6 µM CHIR99021. Cultures presented have been cultured out to day 18.
Figure 15:
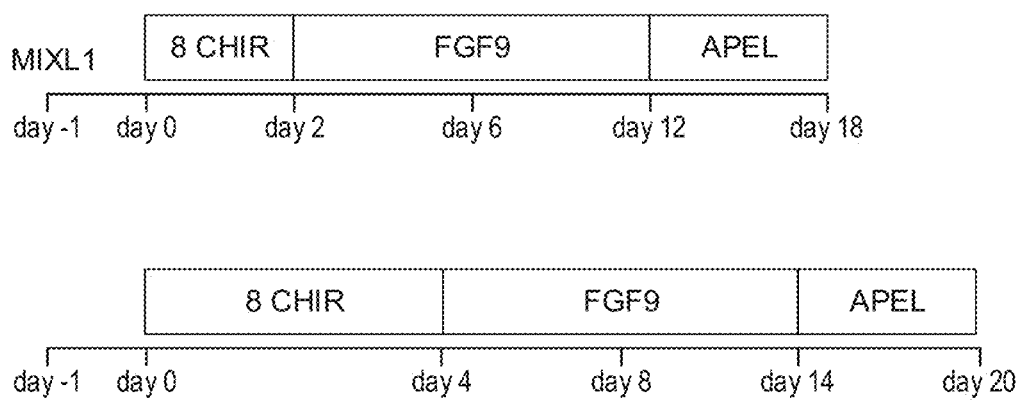
FIG. 15. Diagram outlining the conclusion of optimization of Stage 1 differentiation from pluripotency to posterior primitive streak. The conclusion is that the concentration and duration of initial CHIR99021 induction is likely to vary with individual starting cell and that this will need to be optimized for optimal kidney differentiation.
Figure 16:
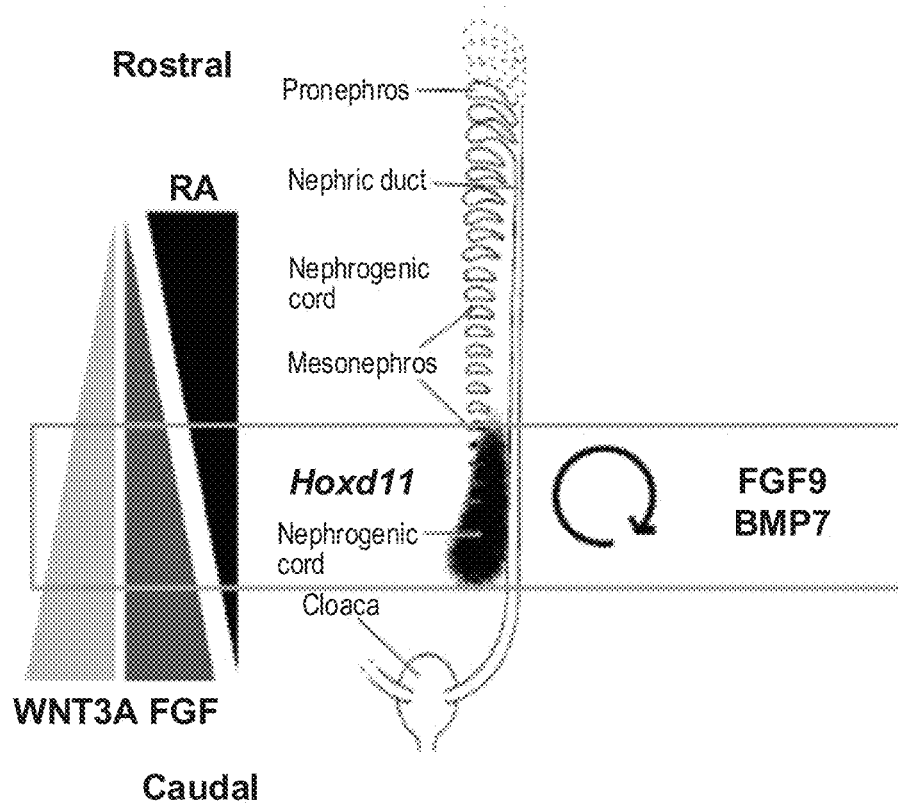
FIG. 16. Diagram outlining the objectives of further optimization steps and the rationale for the inclusion of an antagonist of RA signaling to ensure the generation of an appropriately caudal metanephric mesenchyme population. In short, there is a gradient of RA signaling in the developing embryo such that activity is highest at the cranial end while production of enzymes for the degradation of RA within the caudal tailbud reduces RA signaling at that end of the embryo. The permanent kidney (metanephros) arises at the level of the hindlimbs, and hence is likely to be in a relatively low RA activity zone, whereas the epithelium that gives rise to the ureteric bud arises earlier and hence in a zone of relatively higher RA activity.
Figure 17:
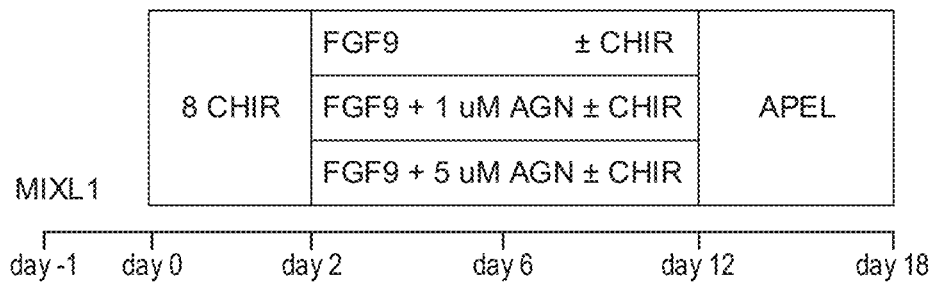
FIG. 17. Diagrammatic representation of the optimization of nephron progenitor induction via the variation of stages 2 and 3 of differentiation. This includes the inclusion of an antagonist of retinoic acid receptor activity, AGN193109, added at either 104 or 504 together with low levels of CHIR99021 (1 µM).
Figure 18:
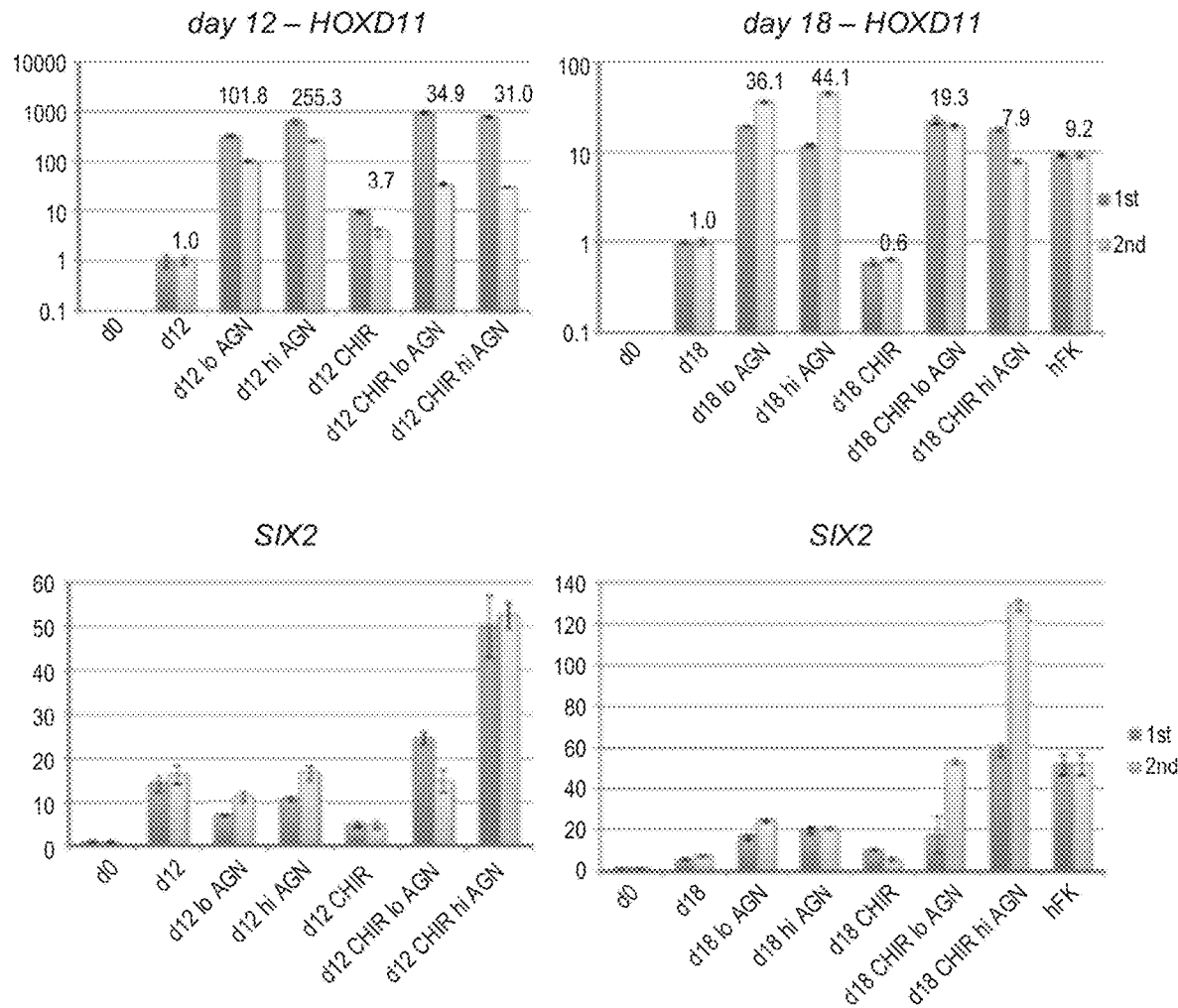
FIG. 18. Quantiative PCR results showing the effect of the additional of CHIR99021 and/or AGN193109 from day 4 of differentiation on the expression of the metanephric mesenchymal markers Hoxd11 and Six2, as assessed at either day 12 or day 18 of differentiation.
Figure 19:
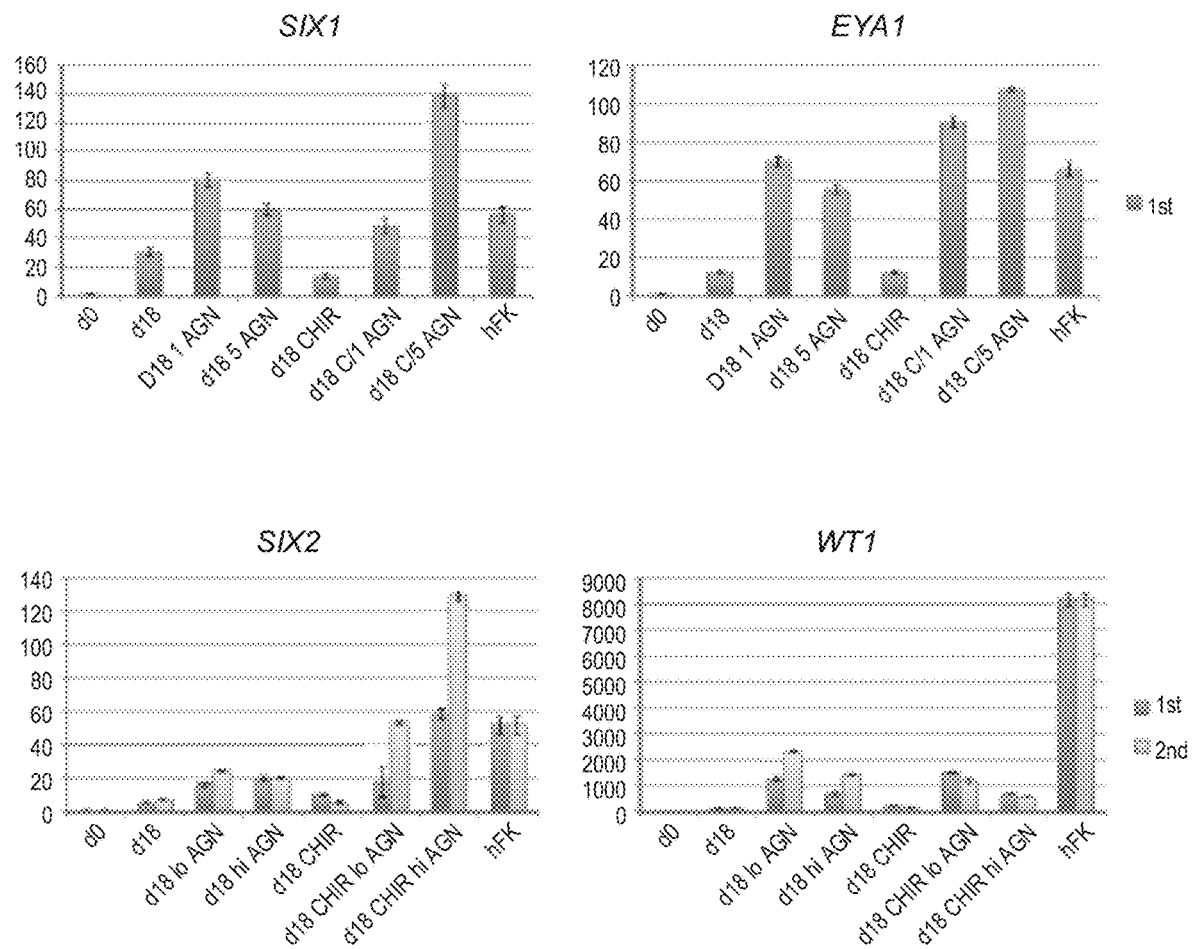
FIG. 19. Quantiative PCR results showing the effect of the additional of CHIR99021 and/or AGN193109 from day 4 of differentiation on the expression of other cap mesenchyme/nephron progenitor markers (Six1, Six2, Eya1, WT1), as assessed at day 18 of differentiation.

We also further analyzed the role of CHIR99021 and found that the more present in the first 2 days in culture, the more ureteric bud is produced with 6 µM being better than 8 µM (FIG. 14). However, a longer time in CHIR99021 (4 versus 2 days) gives more tubular structures versus sheets which ultimately have more mesenchyme that shows an ability to form more mature podocyte markers As summarized on FIG. 15 is that each cell line is likely to also need optimisation for the concentration and duration of CHIR99021 in Stage 1.

In addition, production of mesenchyme is improved if we continue to include CHIR99021 (Wnt agonist used in Stage 1) at 1 µM through Stage 2 and 3 and if we add an antagonist of RA (e.g. AGN193109). This is because we are posteriorising the mesenchyme to be more like metanephros (i.e. gives rise to permanent kidney) versus mesonephros (i.e. regresses during development). We are determining this better mesenchymal outcome in terms of increased HOXD11 expression (more specific to metanephros) and SIX2, SIX1, WT1, EYA1 (i.e all higher in metanephros). We do still produce ureteric epithelium with these present, but perhaps not as much as without these or with RA. This is summarized in FIGS. 16-19. Based on this additional optimisation, it is proposed that different starting cells (e.g. different hPSC from different patients) will vary slightly in their responses to the dose and timing of each stage such that we may need more or less CHIR, RA or RA antagonist, FGF9 and/or BMP7 for each. Thus it is likely that optimization of the response of different patient cell lines will occur cell line by cell line. More importantly, to investigate a patient cell line with a mutation in a gene critical for the nephrons, we may choose to maximise the mesenchyme made (e.g produce more metanephric mesenchyme) by using CHIR99021 and an RA antagonist such as AGN193106 in stage 3 or in stages 2 and 3. Conversely, in a patient with a mutation in a gene affecting the collecting ducts, we might maximise the ureteric epithelium induced (e.g produce more ureteric bud) by having initially less CHIR99021 and adding RA in stage 3.

Figure 20:
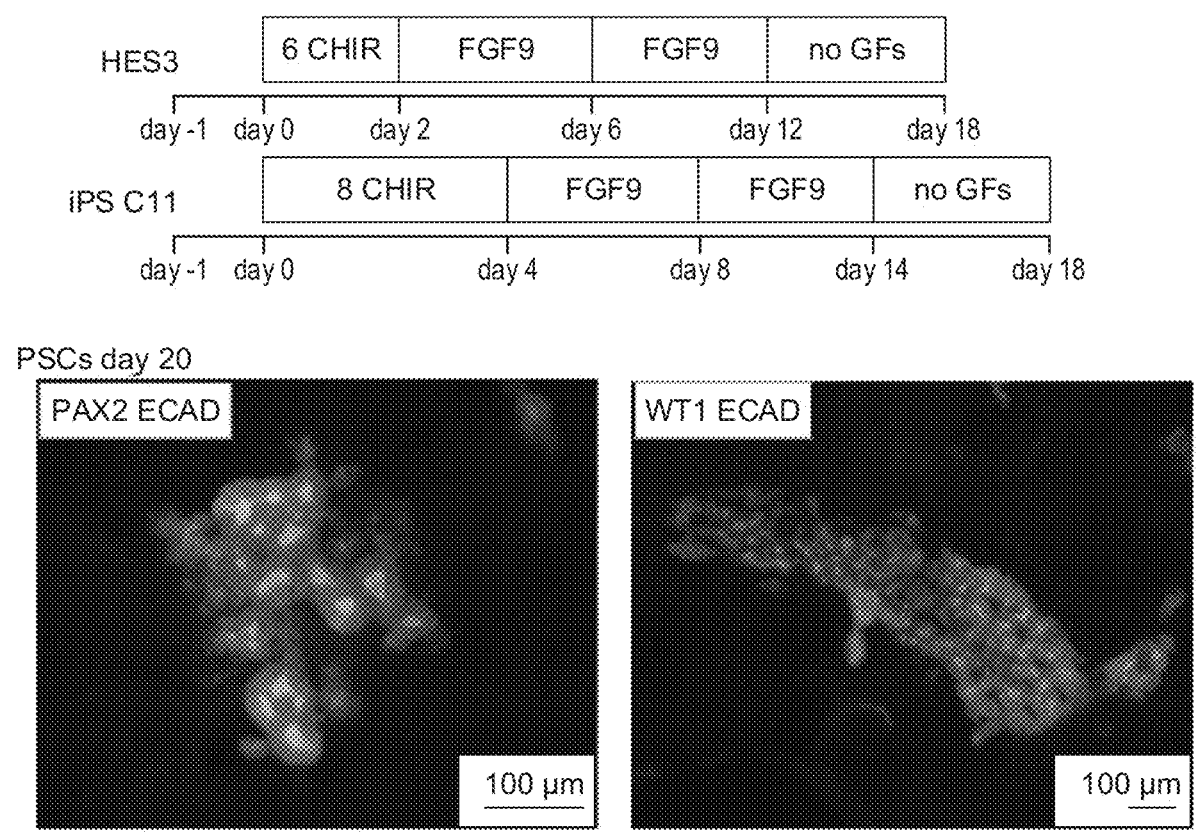
FIG. 20. Directed differentiation of human iPSC cell line C11 to kidney organoids containing nephron progenitors and ureteric epithelium. The protocol used for the differentiation is displayed diagammatically in comparison to that used for the differentiation of the hESC line HES3. This included an additional two days of CHIR99021. Images show the resulting organoids after day 20 of culture. WT1+ mesenchyme (red) surrounds a branching ureteric epithelium (green).
Figure 21:
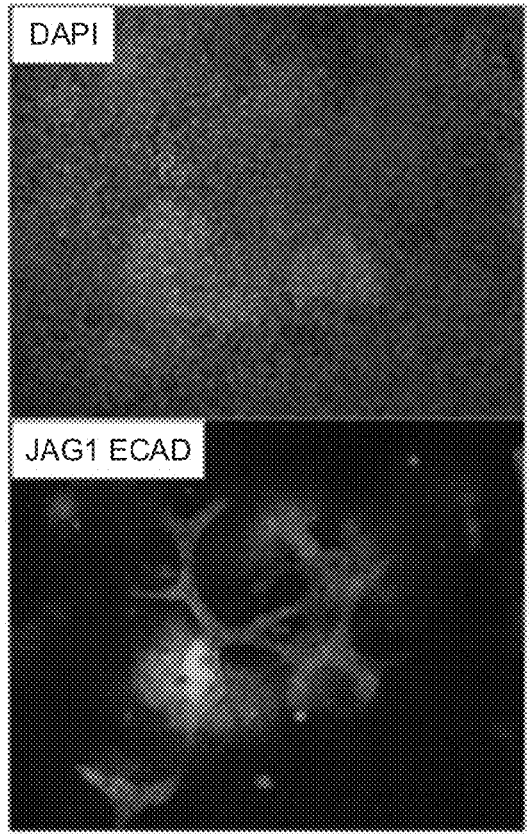
FIG. 21. Directed differentiation of human iPSC cell line C32 to kidney organoids containing nephron progenitors and ureteric epithelium. Images show the resulting organoids after day 18 of culture. WT1+ mesenchyme (red) surrounds a branching ureteric epithelium (green).
Figure 21:
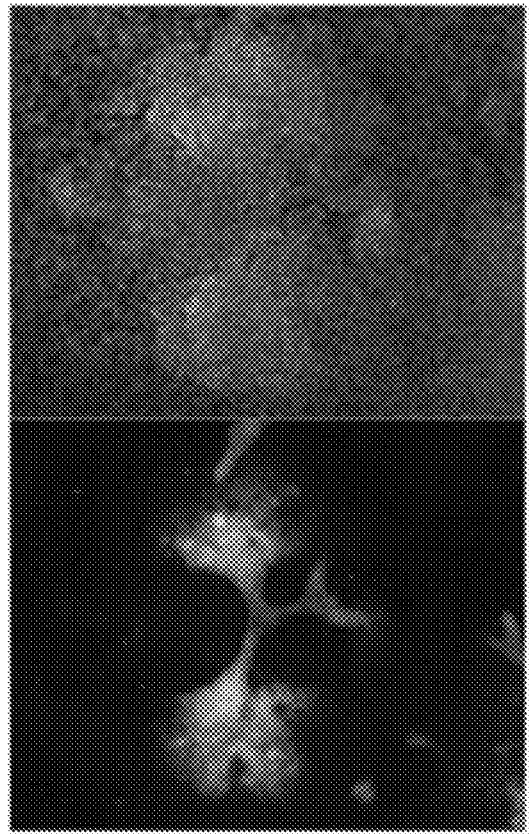

FIGS. 20 and 21 show evidence that the method disclosed herein works on patient-derived iPSCs as well as hESCs. Data is shown from two different patient cells lines.

The capacity of cells to 'self-organise' during both development and wound repair has long been documented[30]. During 'self-organisation', distinct cell types take up specific patterns with respect to each other to create the complex structures that exist within an organ. This process is thought to involve specific cell-cell recognition and is likely to require appropriate ligand-receptor signalling and cell-matrix interactions. Recent studies in which hESCs have been induced to differentiate in culture has revealed that 3D morphogenesis of tissues as complex as optic cup, pituitary or intestine can occur via 'self-organisation' of the component cells[31-33]. This implies a sophisticated capacity for a complex aggregate of cells to pattern or 'self-organise'. Several previous studies have reported the directed differentiation of hESC to IM, podocyte or proximal tubule[6,13,34,35]. None of these reported the simultaneous induction of UB and MM-derived structures or evidence of self-organisation although the growth factor regimes used were similar. Several critical differences exist in our approach. This is the first approach utilising FGF9 which has recently been shown to be critical for MM survival. Loss of FGF9 and FGF20 results in renal agenesis and a lack of FGF9 renders the MM unable to support continued development[20]. We regard this as a critical and defining component of our protocol. Secondly, a stringent requirement for co-expression of combinations of genes/proteins to identify an endpoint, particularly at the stage of IM, has allowed us to more definitively evaluate success. In addition, we have not sorted subpopulations for subsequent differentiation, thereby allowing the influence of surrounding non-target cell types to influence the cultures as a whole. Given the described role of PM and tailbud signalling at various stages of kidney development[36,37], this may have promoted the coordinated differentiation of all communicating cell types required for formation of the kidney.

The described hESC differentiation process generates reciprocally-inducing kidney progenitor populations able to self-organise to form early nephrons. This represents a significant advancement towards the generation of renal tissue from pluripotent cell sources. However, normal kidney development involves a careful balance between the self-renewal of nephron progenitors versus their differentiation into nephrons. The differentiated hESC cultures described here showed the formation of many RVs but the significant loss of nephron progenitors with time, evoking the phenotype of premature progenitor differentiation seen in Six2 mutant mice[3]. This is a key challenge and suggests scope for improvement in the differentiation protocol, potentially requiring alterations to growth factors, extracellular matrix and/or oxygen tension[20,38,39] to more fully reproduce those of the embryonic kidney. A staged shift to organoid culture in bioreactors may also facilitate a more 3D environment.

In summary, here we report the successful differentiation of pluripotent cells to a self-organising kidney. The coordinated induction of cells from the various key cellular populations involved in kidney development again demonstrates the requirement for interacting niches for the creation of complex morphogenetic structures. The capacity for such populations to undergo self-organisation in vitro bodes well for the future of tissue/organ bioengineering. The fact that we can form organoids from differentiated hES cell cultures alone opens the possibility of generating tissue-based nephrotoxicity screens, in vitro disease models or developing transplantable organoids to supplement renal function. It also suggests the feasibility of generating specific mature renal cell types for later purification.

Particular uses of the cells generated using this method may include:
  Generating mini-kidney organoids or purified renal cell for nephrotoxicity screening;
  Generating mini-kidney organoids or purified renal cell for disease modelling, either in general or patient by patient; and/or
  Generating mini-kidney organoids or purified renal cell types for drug screening for the therapeutic treatment of kidney disease.

These could be performed in microbioreactors or after bioprinting into a larger format screen. For disease modelling or drug screening, it is likely we would purify individual cell types and culture them in a manner or format that would provide useful information based upon the specific disease. For example, we might isolate UB and grow in matrigel cultures to assess cyst formation (e.g for diseases such as nephronopthisis) or isolate MM to make podocytes (e.g for diseases such as Finnish nephropathy or Alport syndrome).

Particular examples of cellular therapies and organ replacement or repair may include:
  Generating kidney cell types for cellular therapy (acute kidney injury or chronic kidney injury);
  Generating kidney cell types for whole organ replacement bioengineering, which may need to link together multiple smaller kidneys to form a replacement 'organ'; and/or
  Generating kidney cell types for recellularisation of decellularised scaffolds.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLE 1

Sequences of primers used for RT-PCR

|       | Forward (5'-3')                      | Reverse (5'-3')                      |
|-------|--------------------------------------|--------------------------------------|
| PAX2  | TATGCACTGCAAAGCAGACC (SEQ ID NO. 1)  | GAAAGGCTGCTGAACTTTGG (SEQ ID NO. 20) |
| LHX1  | ATGCAACCTGACCGAGAAGT (SEQ ID NO. 2)  | CAGGTCGCTAGGGGAGATG (SEQ ID NO. 21)  |
| OSR1  | TTCAGCTAAAGCCCCAGAGA (SEQ ID NO. 3)  | CGGCACTTTGGAGAAAGAAG (SEQ ID NO. 22) |
| MIXL1 | GGTACCCCGACATCCACTT (SEQ ID NO. 4)   | TTCAGAGAGAGGGGAACAGG (SEQ ID NO. 23) |

TABLE 1-continued

Sequences of primers used for RT-PCR

| | Forward (5'-3') | Reverse (5'-3') |
|---|---|---|
| T | AGGTACCCAACCCTGAGGAG (SEQ ID NO. 5) | GATGGGTGAGGGGTGTGTAG (SEQ ID NO. 24) |
| CRET | CCGCACACGGCTGCATGAGA (SEQ ID NO. 6) | AAGGTGCCTGGGGGTCGGTT (SEQ ID NO. 25) |
| HOXB7 | CGATGCAGGGCTTGTACCCC (SEQ ID NO. 7) | GGCCTCGTTTGCGGTCAGTT (SEQ ID NO. 26) |
| SIX2 | GCCGAGGCCAAGGAAAGGGAGAA (SEQ ID NO. 8) | AGCAGTGCGGGGCTGGATGA (SEQ ID NO. 27) |
| WT1 | CGCACGGTGTCTTCAGAGGC (SEQ ID NO. 9) | CCTGTATGAGTCCTGGTGTGGGT (SEQ ID NO. 28) |
| GDNF | CTGCCTGGTGCTGCTCCACA (SEQ ID NO. 10) | AGCTGCAGCCTGCCGATTCC (SEQ ID NO. 28) |
| HOXD11 | CCACGGTCAACTCGGGACCT (SEQ ID NO. 11) | TTCCTACAGACCCCGCCGTG (SEQ ID NO. 30) |
| PAX6 | GGCAACCTACGCAAGATGGC (SEQ ID NO. 12) | TGAGGGCTGTGTCTGTTCGG (SEQ ID NO. 31) |
| SYNPO | TCTACCATGGCTACCTGCCT (SEQ ID NO. 13) | TTCCGGGTAGAGAAGGAGGG (SEQ ID NO. 32) |
| NPHS1 | GAGTATGAGTGCCAGGTCGG (SEQ ID NO. 14) | ATGGTGATGTCAGGTGCTGG (SEQ ID NO. 33) |
| AQP1 | GCCGTGACCTTGGTGGCTCA (SEQ ID NO. 15) | TGGCCGCTGGTCCACACCTT (SEQ ID NO. 34) |
| AQP2 | TCTGCTCCATGAGATCACGCCA (SEQ ID NO. 16) | ATCGGTGGAGGCGAAGATGCA (SEQ ID NO. 35) |
| SCNNB1 | CTTCACGAGCAGAGGTCATACC (SEQ ID NO. 17) | GGACCTCAGAACCATTCACGGT (SEQ ID NO. 36) |
| SLC3A1 | TACGGTTCTGGCTCACAAAGGG (SEQ ID NO. 18) | GCTCCGAGTATTGTGTGACCG (SEQ ID NO. 37) |
| GAPDH | CGAGATCCCTCCAAAATCAA (SEQ ID NO. 19) | GTCTTCTGGGTGGCAGTGAT (SEQ ID NO. 38) |

TABLE 2

Sequences of primers used for qRT PCR

| | Forward (5'-3') | Reverse (5'-3') |
|---|---|---|
| SOX17 | ACGCCGAGTTGAGCAAGA (SEQ ID NO. 39) | TCTGCCTCCTCCACGAAG (SEQ ID NO. 58) |
| T | AGGTACCCAACCCTGAGGA (SEQ ID NO. 40) | GCAGGTGAGTTGTCAGAATAGGT (SEQ ID NO. 59) |
| MIXL1 | GGTACCCCGACATCCACTT (SEQ ID NO. 41) | GCCTGTTCTGGAACCATACCT (SEQ ID NO. 60) |
| OSR1 | GGACCTCTGCGGAACAAG (SEQ ID NO. 42) | TGCAGGGAAGGGTGGATA (SEQ ID NO. 61) |
| PAX2 | GCAACCCCGCCTTACTAAT (SEQ ID NO. 43) | AACTAGTGGCGGTCATAGGC (SEQ ID NO. 62) |
| LHX1 | ATGCAACCTGACCGAGAAGT (SEQ ID NO. 44) | CAGGTCGCTAGGGGAGATG (SEQ ID NO. 63) |

TABLE 2-continued

Sequences of primers used for qRT PCR

| | Forward (5'-3') | Reverse (5'-3') |
|---|---|---|
| TBX6 | CATCCACGAGAATTGTACCCG (SEQ ID NO. 45) | AGCAATCCAGTTTAGGGGTGT (SEQ ID NO. 64) |
| PARAXIS | GCGGGCAGTGCCAAGGGCG (SEQ ID NO. 46) | CCCTCACCTTCAAGCAGCTGC (SEQ ID NO. 65) |
| FOXF1 | GCGGCTTCCGAAGGAAATG (SEQ ID NO. 47) | CAAGTGGCCGTTCATCATGC (SEQ ID NO. 66) |
| OCT4 | AGCAAAACCCGGAGGAGT (SEQ ID NO. 48) | CCACATCGGCCTGTGTATATC (SEQ ID NO. 67) |
| NANOG | AAGGCCTCAGCACCTACCTA (SEQ ID NO. 49) | ATTGGAAGGTTCCCAGTCGG (SEQ ID NO. 68) |
| SIX2 | CGCCCATGTGGGTCAGTGGG (SEQ ID NO. 50) | AGCCGGGAGCGCTGTAGTCA (SEQ ID NO. 69) |
| HOXD11 | GCCAGTGTGCTGTCGTTCCC (SEQ ID NO. 51) | CTTCCTACAGACCCCGCCGT (SEQ ID NO. 70) |
| HOXB7 | GCCTACAAATCATCCGGCCA (SEQ ID NO. 52) | GGTTGGAAGCAAACGCACAA (SEQ ID NO. 71) |
| FOXD1 | GACTCTGCACCAAGGGACTG (SEQ ID NO. 53) | CCTCGAGCGCGCTAACATAG (SEQ ID NO. 72) |
| SOX9 | CCGAAAGCGGAGCTCGAAAC (SEQ ID NO. 54) | AGTTTCCGGGGTTGAAACTGG (SEQ ID NO. 73) |
| SF1 | GTGTACCAAGTGTGGAGGGG (SEQ ID NO. 55) | AGGTGCTTCACCCAGTTCAG (SEQ ID NO. 74) |
| GATA6 | CATGACTCCAACTTCCACCT (SEQ ID NO. 56) | ACTTGAGCTCGCTGTTCTCG (SEQ ID NO. 75) |
| GAPDH | AGCCACATCGCTCAGACAC (SEQ ID NO. 57) | GCCCAATACGACCAAATCC (SEQ ID NO. 76) |

REFERENCES

1. Little, M. H. & McMahon, A. P. (2012) Mammalian kidney development: principles, progress, and projections. *Cold Spring Harb Perspect Biol.* 1, 4(5) (2012).
2. Tam, P P., Loebel, D A. Gene function in mouse embryogenesis: get set for gastrulation. *Nat. Rev. Genet.* 8(5), 368-381 (2007).
3. Kobayashi, A., et al. Six2 defines and regulates a multipotent self-renewing nephron progenitor population throughout mammalian kidney development. *Cell Stem Cell* 3, 169-181 (2008).
4. Rumballe, B. A., et al. Nephron formation adopts a novel spatial topology at cessation of nephrogenesis. *Dev. Biol.* 360, 110-122 (2011).
5. Lusis, M., Li, J., Meson, J., Little, M. H. Isolation of clonogenic, long-term self-renewing renal stem cells. *Stem Cell Research* 5, 23-39 (2010).
6. Takasato M., Maier B., Little M H. Recreating kidney progenitors from pluripotent cells. *Pediatr Nephrol.* (2013). Epub ahead of print September 2013
7. Gadue, P., Huber, T L., Paddison, P J., Keller, G M. Wnt and TGF-beta signaling are required for the induction of an in vitro model of primitive streak formation using embryonic stem cells. *Proc Natl Acad Sci USA* 103(45), 16806-16811 (2006).
8. Soares, M L., et al. Functional studies of signaling pathways in peri-implantation development of the mouse embryo by RNAi. *BMC Dev. Biol.* 5, 28 (2005).
9. Lu, C. C. & Robertson, E. J. Multiple roles for Nodal in the epiblast of the mouse embryo in the establishment of anterior-posterior patterning. *Dev. Biol.* 273, 149-159 (2004).
10. Sumi, T., Tsuneyoshi, N., Nakatsuji, N., Suemori, H. Defining early lineage specification of human embryonic stem cells by the orchestrated balance of canonical Wnt/beta-catenin, Activin/Nodal and BMP signaling. *Development* 135(17), 2969-2979 (2008).
11. Davis, R. P., et al. Targeting a GFP reporter gene to the MIXL1 locus of human embryonic stem cells identifies human primitive streak-like cells and enables isolation of primitive hematopoietic precursors. *Blood* 111(4), 1876-1884 (2008).
12. Ng, E S., Davis, R., Stanley, E G., Elefanty, A G. A protocol describing the use of a recombinant protein-based, animal product-free medium (APEL) for human embryonic stem cell differentiation as spin embryoid bodies. *Nat Protoc.* 3(5), 768-776 (2008).
13. Mae S., et al. Monitoring and robust induction of nephrogenic intermediate mesoderm from human pluripotent stem cells. *Nat Commun.* 4, 1367 (2013).
14. James, R G., et al. Odd-skipped related 1 is required for development of the metanephric kidney and regulates formation and differentiation of kidney precursor cells. *Development* 133(15), 2995-3004 (2006).
15. Tsang, T E., et al. Lim1 activity is required for intermediate mesoderm differentiation in the mouse embryo. *Dev. Biol.* 223(1), 77-90 (2000).

16. Tones, M., Gomez-Pardo, E., Dressler, G R., Gruss, P. Pax-2 controls multiple steps of urogenital development. *Development* 121(12), 4057-4065 (1995).
17. Crossley, P H, Martin, G R. The mouse Fgf8 gene encodes a family of polypeptides and is expressed in regions that direct outgrowth and patterning in the developing embryo. *Development* 121(2), 439-451 (1995).
18. Colvin, J S., et al. Genomic organization and embryonic expression of the mouse fibroblast growth factor 9 gene. *Dev Dyn.* 216(1), 72-88 (1999).
19. Dudley, A. T., Godin, R. E., Robertson, E. J. Interaction between FGF and BMP signalling pathways regulates development of metanephric mesenchyme. *Genes Dev.* 13(12), 1601-1613 (1999).
20. Barak, H., et al. FGF9 and FGF20 maintain the stemness of nephron progenitors in mice and man. *Dev Cell* 22(6), 1191-1207 (2012).
21. James, R G., Schultheiss, T M. Bmp signalling promotes intermediate mesoderm gene expression in a dose-dependent, cell-autonomous and translation-dependent manner. *Dev Biol.* 288(1), 113-125 (2005).
22. Rosselot C, et al. Non-cell-autonomous retinoid signalling is crucial for renal development. *Development* 137(2), 283-292 (2010).
23. Kim, D., Dressler, G. R. Nephrogenic factors promote differentiation of mouse embryonic stem cells into renal epithelia. *J Am. Soc. Nephrol.* 16(12), 3527-3534 (2005)
24. Mugford, J. W., et al. Hoxd11 specifies a program of metanephric kidney development within the intermediate mesoderm of the mouse embryo. *Dev. Biol.* 319(2), 396-405 (2008).
25. Pachnis, V., Mankoo, B., Costantini, F. Expression of the c-ret proto-oncogene during mouse embryogenesis. *Development* 119(4), 1005-1017 (1993).
26. Srinivas, S., et al. Expression of green fluorescent protein in the ureteric bud of transgenic mice: a new tool for the analysis of ureteric bud morphogenesis. *Dev. Genet.* 24(3-4), 241-251 (1999).
27. Mendelsohn, C., et al. Stromal cells mediate retinoid-dependent functions essential for renal development. *Development* 126(6), 1139-1148 (1999).
28. Davies, J. A., et al. Dissociation of embryonic kidney followed by re-aggregation as a method for chimeric analysis. *Methods Mol. Biol.* 886, 135-146 (2012).
29. Hendry, C E, Vanslambrouck, J M, et al. Direct transcriptional reprogramming of adult cells to embryonic nephron progenitors. *J Am Soc Nephrol* 24(9), 1424-1434 (2013).
30. Trinkaus, J. P., Groves, P. W. Differentiation in culture of mixed aggregates of dissociated tissue cells. *Proc. Natl. Acad. Sci. USA* 41, 787-795 (1955).
31. Suga, H., et al. Self-formation of functional adenohypophysis in three-dimensional culture. *Nature* 480(7375), 57-62 (2011).
32. Eiraku, M., et al. Self-organizing optic-cup morphogenesis in three-dimensional culture. *Nature* 472(7341), 51-56 (2011).
33. Spence, J. R., et al. Directed differentiation of human pluripotent stem cells into intestinal tissue in vitro. *Nature* 470, 105-108 (2011).
34. Narayanan K., et al. Human embryonic stem cells differentiate into functional renal proximal tubular-like cells. *Kidney Int.* 83(4), 593-603 (2013).
35. Song B., et al. The directed differentiation of human iPS cells into kidney podocytes. *PLoS One.* 7(9), e46453 (2012).
36. Brenner-Anantharam A., et al. Tailbud-derived mesenchyme promotes urinary tract segmentation via BMP4 signaling. *Development* 134(10), 1967-1975 (2007).
37. Guillaume R., Bressan M., Herzlinger D. Paraxial mesoderm contributes stromal cells to the developing kidney. *Dev Biol.* 329(2), 169-175 (2009).
38. Uchiyama Y., et al. Kif26b, a kinesin family gene, regulates adhesion of the embryonic kidney mesenchyme. *Proc. Natl. Acad. Sci. USA* 107(20), 9240-9245 (2010).
39. Linton J M., Martin G R., Reichardt L F. The ECM protein nephronectin promotes kidney development via integrin alpha8beta1-mediated stimulation of Gdnf expression. *Development* 134(13), 2501-2509 (2007).

The invention claimed is:

1. A method of determining the nephrotoxicity of one or a plurality of compounds, comprising:
   (a) producing nephron progenitor cells and ureteric epithelial progenitor cells comprising:
      (i) contacting posterior primitive streak cells with fibroblast growth factor 9 (FGF9) or FGF9 in combination with at least one of fibroblast growth factor 2 (FGF2) and fibroblast growth factor 20 (FGF20);
      (ii) culturing the contacted posterior primitive streak cells for a period of time sufficient for the contacted posterior primitive streak cells to differentiate into intermediate mesoderm (IM) cells;
      (iii) contacting the IM cells with: FGF9 and/or FGF20; and optionally, one or more selected from the group consisting of: bone morphogenic protein 7 (BMP7); heparin; a Wnt (Wingless-related integration site) agonist; retinoic acid (RA), analog or agonist; and an RA antagonist; and
      (iv) culturing the contacted IM cells for a period of time sufficient for the contacted IM cells to differentiate into nephron progenitor cells and ureteric epithelial progenitor cells;
   (b) isolating, enriching, or purifying the nephron progenitor cells and/or ureteric epithelial progenitor cells; and
   (c) contacting the one or plurality of compounds with the isolated, enriched, or purified nephron progenitor cells and/or ureteric epithelial progenitor cells to determine whether or not the one or plurality of compounds is nephrotoxic.

2. The method of claim 1, wherein the FGF9 and/or FGF20 is at a concentration in the range of 20 ng to 1 µg/mL; wherein the BMP7 is present at a concentration in the range of 25 to 75 ng/ml; wherein the RA, analog or agonist is present at a concentration in the range of 10 pM to 1 µM; wherein the RA antagonist is present at a concentration in the range of 0.50 pM to 10 µM; and wherein the Wnt agonist is present at a concentration in the range of 0.1 µM to 10 µM.

3. The method of claim 1, wherein the IM cells are further contacted with heparin at a concentration in the range of 0.1-10 µg/mL.

4. The method of claim 1, wherein the nephron progenitor cells and ureteric epithelial progenitor cells are produced synchronously or simultaneously from the IM cells.

5. The method of claim 1, further comprising contacting human pluripotent stem cells (hPSCs) with at least one of BMP4, Activin A and a Wnt agonist, and culturing the contacted hPSCs for a period of time sufficient for the contacted hPSCs to differentiate into posterior primitive streak cells.

6. The method of claim 5, wherein the hPSCs are human embryonic stem cells or induced human pluripotent stem cells.

7. The method of claim 5, wherein (i) the BMP4 is at a concentration of 5-40 ng/ml; (ii) the Activin A is at a concentration of 3-40 ng/ml; and the Wnt agonist is at a concentration in the range of 0.5 to 50 µM.

8. A method of determining the nephrotoxicity of one or a plurality of compounds, comprising:
   (a) producing nephron progenitor cells and ureteric epithelial progenitor cells comprising in sequence comprising:
      (i) contacting human pluripotent stem cells (hPSCs) with a Wnt agonist;
      (ii) culturing the contacted hPSCs for a period of time sufficient for the contacted hPSCs to differentiate into posterior primitive streak cells;
      (iii) contacting the posterior primitive streak cells with FGF9 or FGF9 with an RA antagonist;
      (iv) culturing the contacted posterior primitive streak cells for a period of time sufficient for the contacted posterior primitive streak cells to differentiate into IM cells;
      (v) contacting the IM cells with FGF9 alone or in combination with one or more of BMP7; RA; an RA antagonist; a Wnt agonist; FGF20; and heparin; and
      (vi) culturing the contacted IM cells for a period of time sufficient for the contacted IM cells to differentiate into nephron progenitor cells and ureteric epithelial progenitor cells;
   (b) isolating, enriching, or purifying the nephron progenitor cells and/or ureteric epithelial progenitor cells; and
   (c) contacting the one or plurality of compounds with the isolated, enriched, or purified nephron progenitor cells and/or ureteric epithelial progenitor cells to determine whether or not the one or plurality of compounds is nephrotoxic.

9. The method of claim 8, wherein at the least one of the FGF9, FGF2 and FGF20 are at a concentration of 100 to 400 ng/mL.

10. A method of determining the nephrotoxicity of one or a plurality of compounds, comprising:
 (a) producing nephron progenitor cells and ureteric epithelial progenitor cells comprising:
  (i) contacting posterior primitive streak cells with fibroblast growth factor 9 (FGF9) or FGF9 in combination with at least one of fibroblast growth factor 2 (FGF2) and fibroblast growth factor 20 (FGF20);
  (ii) culturing the contacted posterior primitive streak cells for a period of time sufficient for the contacted posterior primitive streak cells to differentiate into intermediate mesoderm (IM) cells;
  (iii) contacting the IM cells with: FGF9 and/or FGF20; and optionally, one or more selected from the group consisting of: bone morphogenic protein 7 (BMP7); heparin; a Wnt agonist; retinoic acid (RA), analog or agonist; and an RA antagonist; and
  (iv) culturing the contacted IM cells for a period of time sufficient for the contacted IM cells to differentiate into nephron progenitor cells and ureteric epithelial progenitor cells;
 (b) isolating, enriching, or purifying the nephron progenitor cells and/or ureteric epithelial progenitor cells; and
 (c) differentiating the isolated, enriched, or purified nephron progenitor cells and/or ureteric epithelial progenitor cells to produce renal organoids, kidney cells, or kidney tissue; and
 (d) contacting the one or plurality of compounds with the renal organoids, kidney cells, or kidney tissue to determine whether or not the one or plurality of compounds is nephrotoxic.

11. The method of claim 10, wherein the FGF9 and/or FGF20 is at a concentration in the range of 20 ng to 1 µg/mL; wherein the BMP7 is present at a concentration in the range of 25 to 75 ng/ml; wherein the RA, analog or agonist is present at a concentration in the range of 10 pM to 1 µM; wherein the RA antagonist is present at a concentration in the range of 0.50 pM to 10 µM; and wherein the Wnt agonist is present at a concentration in the range of 0.1 µM to 10 µM.

12. The method of claim 10, wherein the IM cells are further contacted with heparin at a concentration in the range of 0.1-10 µg/mL.

13. The method of claim 10, wherein the nephron progenitor cells and ureteric epithelial progenitor cells are produced synchronously or simultaneously from the IM cells.

14. The method of claim 10, further comprising contacting human pluripotent stem cells (hPSCs) with at least one of BMP4, Activin A and a Wnt agonist, and culturing the contacted hPSCs for a period of time sufficient for the contacted hPSCs to differentiate into posterior primitive streak cells.

15. The method of claim 14, wherein the hPSCs are human embryonic stem cells or induced human pluripotent stem cells.

16. The method of claim 14, wherein (i) the BMP4 is at a concentration of 5-40 ng/mL; (ii) the Activin A is at a concentration of 3-40 ng/ml; and the Wnt agonist is at a concentration in the range of 0.5 to 50 µM.

17. A method of determining the nephrotoxicity of one or a plurality of compounds, comprising:
 (a) producing nephron progenitor cells and ureteric epithelial progenitor cells comprising in sequence comprising:
  (i) contacting human pluripotent stem cells (hPSCs) with a Wnt agonist;
  (ii) culturing the contacted hPSCs for a period of time sufficient for the contacted hPSCs to differentiate into posterior primitive streak cells;
  (iii) contacting the posterior primitive streak cells with FGF9 or FGF9 with an RA antagonist;
  (iv) culturing the contacted posterior primitive streak cells for a period of time sufficient for the contacted posterior primitive streak cells to differentiate into IM cells;
  (v) contacting the IM cells with FGF9 alone or in combination with one or more of BMP7; RA; an RA antagonist; a Wnt agonist; FGF20; and heparin; and
  (vi) culturing the contacted IM cells for a period of time sufficient for the contacted IM cells to differentiate into nephron progenitor cells and ureteric epithelial progenitor cells;
 (b) isolating, enriching, or purifying the nephron progenitor cells and/or ureteric epithelial progenitor cells; and
 (c) differentiating the isolated, enriched, or purified nephron progenitor cells and/or ureteric epithelial progenitor cells to produce renal organoids, kidney cells, or kidney tissue; and
 (d) contacting the one or plurality of compounds with the renal organoids, kidney cells, or kidney tissue to determine whether or not the one or plurality of compounds is nephrotoxic.

18. The method of claim 17, wherein at the least one of the FGF9, FGF2 and FGF20 are at a concentration of 100 to 400 ng/mL.

* * * * *

UNITED STATES PATENT AND TRADEMARK OFFICE
CERTIFICATE OF CORRECTION

PATENT NO. : 12,060,580 B2  
APPLICATION NO. : 17/155631  
DATED : August 13, 2024  
INVENTOR(S) : Melissa Little et al.

Page 1 of 1

It is certified that error appears in the above-identified patent and that said Letters Patent is hereby corrected as shown below:

In the Claims

Column 51, Claim 2, Line 57, delete "ng/ml;" and insert --ng/mL;--.

Column 52, Claim 7, Line 32, delete "ng/ml;" and insert --ng/mL;--.

Column 52, Claim 7, Line 33, delete "ng/ml;" and insert --ng/mL;--.

Column 53, Claim 11, Line 35, delete "ng/ml;" and insert --ng/mL;--.

Column 54, Claim 16, Line 10, delete "ng/ml;" and insert --ng/mL;--.

Signed and Sealed this  
Seventh Day of October, 2025

John A. Squires  
*Director of the United States Patent and Trademark Office*